(12) United States Patent
Walsh et al.

(10) Patent No.: US 9,931,143 B2
(45) Date of Patent: Apr. 3, 2018

(54) BONE STABILIZATION DEVICE AND METHODS OF USE

(71) Applicant: NEWSOUTH INNOVATIONS PTY LIMITED, Sydney, New South Wales (AU)

(72) Inventors: William Robert Walsh, Maroubra (AU); Matthew Henry Pelletier, Maroubra (AU)

(73) Assignee: NEW SOUTH INNOVATIONS PTY LIMITED, Sydney (AU)

( * ) Notice: Subject to any disclaimer, the term of this patent is extended or adjusted under 35 U.S.C. 154(b) by 72 days.

(21) Appl. No.: 14/424,408

(22) PCT Filed: Aug. 30, 2013

(86) PCT No.: PCT/AU2013/000984
§ 371 (c)(1),
(2) Date: Feb. 26, 2015

(87) PCT Pub. No.: WO2014/032118
PCT Pub. Date: Mar. 6, 2014

(65) Prior Publication Data
US 2015/0335363 A1 Nov. 26, 2015

(30) Foreign Application Priority Data
Aug. 31, 2012 (AU) ................................ 2012903797

(51) Int. Cl.
*A61B 17/70* (2006.01)

(52) U.S. Cl.
CPC .......... *A61B 17/7071* (2013.01); *A61B 17/70* (2013.01); *A61B 17/707* (2013.01)

(58) Field of Classification Search
CPC ............................ A61B 17/70; A61B 17/7071
See application file for complete search history.

(56) References Cited

U.S. PATENT DOCUMENTS

| 5,330,472 A | 7/1994 | Stavenhagen |
| 5,527,311 A | 6/1996 | Procter et al. |
| 5,645,084 A | 7/1997 | McKay |

(Continued)

FOREIGN PATENT DOCUMENTS

| AU | 769376 B2 | 1/2004 |
| AU | 2011203024 A1 | 7/2011 |

(Continued)

OTHER PUBLICATIONS

CN Search Report dated Jun. 27, 2016 as received in Application No. 2013800455246.

(Continued)

*Primary Examiner* — Ellen C Hammond
*Assistant Examiner* — Stuart S Bray
(74) *Attorney, Agent, or Firm* — Maschoff Brennan

(57) ABSTRACT

Technologies are generally provided for devices and methods for use in bone fixation, bone fusion and/or bone stabilization. In various embodiments, the devices and methods relate to a bone stabilization having a first end, second end and a bridge connecting the first and second ends. The first end has a bone engagement feature and may be fused to bone over time without the use of osteogenic materials.

20 Claims, 35 Drawing Sheets

(56) References Cited

U.S. PATENT DOCUMENTS

| | | | |
|---|---|---|---|
| 5,782,919 A | 7/1998 | Zdeblick et al. | |
| 6,346,123 B1 | 2/2002 | McKay | |
| 6,547,795 B2 | 4/2003 | Schneiderman | |
| 6,565,571 B1 | 5/2003 | Jackowski et al. | |
| 6,585,769 B1 | 7/2003 | Muhanna et al. | |
| 6,626,944 B1* | 9/2003 | Taylor | A61B 17/7062 606/249 |
| 6,719,795 B1 | 4/2004 | Cornwall et al. | |
| 6,752,831 B2 | 6/2004 | Sybert et al. | |
| 7,074,239 B1 | 7/2006 | Cornwall et al. | |
| 7,261,738 B2 | 8/2007 | Casey | |
| 7,501,073 B2 | 3/2009 | Wen et al. | |
| 7,611,526 B2 | 11/2009 | Carl et al. | |
| 7,662,186 B2 | 2/2010 | Bagga et al. | |
| 7,666,208 B1 | 2/2010 | Asfora | |
| 7,722,647 B1 | 5/2010 | Wang et al. | |
| 7,722,895 B1 | 5/2010 | McKay et al. | |
| 7,780,709 B2 | 8/2010 | Bruneau et al. | |
| 7,789,898 B2* | 9/2010 | Peterman | A61B 17/707 606/246 |
| D643,927 S | 8/2011 | Prasad et al. | |
| 8,034,079 B2* | 10/2011 | Bruneau | A61B 17/7062 606/249 |
| 8,133,261 B2 | 3/2012 | Fisher et al. | |
| 8,197,513 B2 | 6/2012 | Fisher et al. | |
| 8,221,461 B2 | 7/2012 | Kuiper et al. | |
| 8,262,696 B2 | 9/2012 | Falahee | |
| 8,303,879 B2 | 11/2012 | Bertele et al. | |
| 8,308,771 B2 | 11/2012 | Bennett et al. | |
| 8,353,912 B2 | 1/2013 | Darian et al. | |
| 8,372,118 B2 | 2/2013 | Chin et al. | |
| 8,377,097 B2 | 2/2013 | Gordon et al. | |
| 8,529,606 B2 | 9/2013 | Alamin et al. | |
| 8,579,941 B2 | 11/2013 | Chervitz et al. | |
| 8,758,408 B2* | 6/2014 | Chin | A61B 17/7065 606/248 |
| 2001/0014831 A1 | 8/2001 | Scarborough | |
| 2004/0259972 A1 | 12/2004 | Ringeisen et al. | |
| 2005/0080486 A1 | 4/2005 | Fallin et al. | |
| 2005/0131412 A1 | 6/2005 | Olevsky et al. | |
| 2005/0203512 A1 | 9/2005 | Hawkins et al. | |
| 2005/0203624 A1 | 9/2005 | Serhan et al. | |
| 2006/0089645 A1 | 4/2006 | Eckman | |
| 2006/0136060 A1 | 6/2006 | Taylor | |
| 2006/0190081 A1 | 8/2006 | Kraus et al. | |
| 2006/0224159 A1 | 10/2006 | Anderson | |
| 2006/0241613 A1* | 10/2006 | Bruneau | A61B 17/7062 606/249 |
| 2006/0247623 A1 | 11/2006 | Anderson et al. | |
| 2006/0247634 A1 | 11/2006 | Warner et al. | |
| 2006/0247650 A1 | 11/2006 | Yerbs et al. | |
| 2006/0271055 A1* | 11/2006 | Thramann | A61B 17/7053 606/74 |
| 2006/0276788 A1 | 12/2006 | Berry et al. | |
| 2006/0293662 A1 | 12/2006 | Boyer et al. | |
| 2007/0016204 A1 | 1/2007 | Martinez et al. | |
| 2007/0049941 A1 | 3/2007 | Thramann | |
| 2007/0083266 A1 | 4/2007 | Lang | |
| 2007/0161990 A1* | 7/2007 | Hillyard | A61B 17/7056 606/86 A |
| 2007/0179611 A1 | 8/2007 | DiPoto et al. | |
| 2007/0191833 A1 | 8/2007 | Bruneau et al. | |
| 2007/0225812 A1 | 9/2007 | Gill | |
| 2007/0233062 A1 | 10/2007 | Berry | |
| 2007/0239278 A1 | 10/2007 | Heinz | |
| 2007/0270844 A1 | 11/2007 | Lin et al. | |
| 2007/0288014 A1* | 12/2007 | Shadduck | A61B 17/68 606/279 |
| 2008/0021476 A1 | 1/2008 | Kirschman | |
| 2008/0091198 A1 | 4/2008 | Leibel et al. | |
| 2008/0109003 A1* | 5/2008 | Peckham | A61B 17/70 606/94 |
| 2008/0114357 A1* | 5/2008 | Allard | A61B 17/707 606/249 |
| 2008/0161810 A1 | 7/2008 | Melkent | |
| 2008/0177264 A1 | 7/2008 | Alamin et al. | |
| 2008/0215096 A1 | 9/2008 | Nash et al. | |
| 2008/0228225 A1 | 9/2008 | Trautwein et al. | |
| 2008/0234824 A1 | 9/2008 | Youssef et al. | |
| 2008/0281423 A1* | 11/2008 | Sheffer | A61B 17/7062 623/17.11 |
| 2008/0300685 A1 | 12/2008 | Carls et al. | |
| 2008/0306554 A1 | 12/2008 | Mckinley | |
| 2009/0005819 A1 | 1/2009 | Ben-Mokhtar et al. | |
| 2009/0036925 A1 | 2/2009 | Sala et al. | |
| 2009/0054931 A1 | 2/2009 | Metz-Stavenhagen | |
| 2009/0112326 A1 | 4/2009 | Lehuec et al. | |
| 2009/0131986 A1 | 5/2009 | Lee et al. | |
| 2009/0163920 A1 | 6/2009 | Hochschuler et al. | |
| 2009/0163958 A1 | 6/2009 | Tarcha et al. | |
| 2009/0182429 A1 | 7/2009 | Humphreys et al. | |
| 2009/0246244 A1 | 10/2009 | Mckay et al. | |
| 2009/0248079 A1 | 10/2009 | Kwak et al. | |
| 2009/0264929 A1 | 10/2009 | Alamin et al. | |
| 2009/0292314 A1 | 11/2009 | Mangione et al. | |
| 2009/0306716 A1 | 12/2009 | Beger et al. | |
| 2010/0010548 A1 | 1/2010 | Ochoa | |
| 2010/0030269 A1 | 2/2010 | Taylor | |
| 2010/0070038 A1 | 3/2010 | Taylor | |
| 2010/0082067 A1 | 4/2010 | Kondrashov | |
| 2010/0094426 A1 | 4/2010 | Grohowski, Jr. et al. | |
| 2010/0121381 A1 | 5/2010 | Berta et al. | |
| 2010/0131008 A1* | 5/2010 | Overes | A61B 17/7062 606/247 |
| 2010/0152779 A1 | 6/2010 | Allard et al. | |
| 2010/0249840 A1 | 9/2010 | Tanaka | |
| 2010/0312278 A1 | 12/2010 | Linares | |
| 2010/0312343 A1 | 12/2010 | Linares | |
| 2011/0022091 A1 | 1/2011 | Anderson et al. | |
| 2011/0029020 A1 | 2/2011 | Gordon et al. | |
| 2011/0040330 A1 | 2/2011 | Sheffer | |
| 2011/0040383 A1* | 2/2011 | Wurfel | A61B 17/7065 623/17.11 |
| 2011/0106263 A1 | 5/2011 | Eisermann | |
| 2011/0125264 A1* | 5/2011 | Bagga | A61B 17/68 623/16.11 |
| 2011/0137353 A1 | 6/2011 | Buttermann | |
| 2011/0172711 A1 | 7/2011 | Kirschman | |
| 2011/0190818 A1 | 8/2011 | Douget | |
| 2011/0208244 A1 | 8/2011 | Shin | |
| 2011/0218572 A1* | 9/2011 | Lechmann | A61B 17/7062 606/249 |
| 2011/0307010 A1 | 12/2011 | Pradhan | |
| 2011/0319935 A1 | 12/2011 | Moskowitz et al. | |
| 2012/0010662 A1 | 1/2012 | O'Neil et al. | |
| 2012/0016418 A1 | 1/2012 | Chin et al. | |
| 2012/0016420 A1* | 1/2012 | Naraghi | A61B 17/7064 606/250 |
| 2012/0046749 A1* | 2/2012 | Tatsumi | A61B 17/1757 623/17.16 |
| 2012/0065683 A1 | 3/2012 | Kuo et al. | |
| 2012/0109202 A1 | 5/2012 | Kretzer et al. | |
| 2012/0143337 A1 | 6/2012 | Jensen et al. | |
| 2012/0165872 A1 | 6/2012 | Alamin et al. | |
| 2012/0215260 A1* | 8/2012 | Paul | A61B 17/7053 606/249 |
| 2012/0226314 A1 | 9/2012 | Chin et al. | |
| 2012/0265250 A1 | 10/2012 | Ali | |
| 2012/0277801 A1 | 11/2012 | Marik et al. | |
| 2013/0035761 A1* | 2/2013 | Sharkey | A61B 17/56 623/17.11 |
| 2013/0123850 A1 | 5/2013 | Schoenefeld et al. | |
| 2013/0144386 A1 | 6/2013 | Horton et al. | |
| 2013/0184751 A1* | 7/2013 | Siegfried | A61B 17/7068 606/248 |
| 2013/0184826 A1 | 7/2013 | Thaiyananthan | |
| 2013/0190820 A1* | 7/2013 | Siegfried | A61B 17/7068 606/248 |
| 2013/0211524 A1* | 8/2013 | Hugues | A61F 2/44 623/17.11 |
| 2013/0244942 A1 | 9/2013 | Benedict et al. | |
| 2013/0325068 A1 | 12/2013 | Fielding et al. | |

(56) References Cited

U.S. PATENT DOCUMENTS

| | | | |
|---|---|---|---|
| 2013/0338720 | A1 | 12/2013 | Kleiner |
| 2014/0012326 | A1 | 1/2014 | Alamin et al. |
| 2014/0025114 | A1 | 1/2014 | Kim et al. |
| 2014/0032118 | A1 | 1/2014 | Yarus et al. |
| 2014/0039558 | A1 | 2/2014 | Alamin et al. |
| 2014/0066987 | A1 | 3/2014 | Hestad et al. |
| 2014/0277499 | A1* | 9/2014 | Ainsworth ............. A61B 17/70 623/17.16 |
| 2014/0336705 | A1 | 11/2014 | Buttermann |
| 2016/0081811 | A1* | 3/2016 | McKay ...................... A61F 2/44 623/17.13 |

FOREIGN PATENT DOCUMENTS

| | | |
|---|---|---|
| AU | 2013206209 A1 | 6/2013 |
| CN | 2782033 Y | 5/2006 |
| CN | 101330885 A | 12/2008 |
| CN | 201208298 Y | 3/2009 |
| CN | 101444435 B | 12/2010 |
| CN | 201719361 U | 1/2011 |
| CN | 201861801 U | 6/2011 |
| EP | 0149540 A2 | 7/1985 |
| EP | 461374 A1 | 12/1991 |
| EP | 0532421 A1 | 3/1993 |
| EP | 0701803 A1 | 3/1996 |
| EP | 1809214 A2 | 7/2007 |
| EP | 1844798 A1 | 10/2007 |
| EP | 0996385 B1 | 1/2008 |
| JP | 3608943 B2 | 1/2005 |
| JP | 2005021420 A | 1/2005 |
| WO | 0003653 A2 | 1/2000 |
| WO | 2006/113814 A2 | 10/2006 |
| WO | 2006/119235 A1 | 11/2006 |
| WO | 2007/070819 A2 | 6/2007 |
| WO | 2008/061055 A2 | 5/2008 |
| WO | 2009/056612 A2 | 5/2009 |
| WO | 2010/048396 A2 | 4/2010 |
| WO | 2010104935 A1 | 9/2010 |
| WO | 2012/006064 A1 | 1/2012 |
| WO | 2012006064 A1 | 1/2012 |
| WO | 2014032118 A1 | 3/2014 |

OTHER PUBLICATIONS

"Aesculap Implant Systems Launches PL-AGE® Anterior Cervical Fusion System," accessed at http://news.cision.com/aesculap/r/aesculap-implant-systems-launches-pl-age--anterior-cervical-fusion-system,c9382058 , Mar. 8, 2013, pp. 1-5.

"Anterior Cervical Plate(cervical Spine Fixation System)," accessed at http://www.alibaba.com/product-detail/Anterior-cervical-plate-cervical-spine-fixation_614171434.html, accessed on Sep. 20, 2014, pp. 1-4.

"clspinedisc," accessed at http://www.ackermannmedical.com/#!cspine-disc-en/c1l3c, accessed on Feb. 3, 2015, pp. 2.

"DTRAX, by Providence Medical Technology," accessed at https://web.archive.org/web/20131101022739/http://providencemt.com/procedure, accessed on Sep. 20, 2014, pp. 1-2.

"InterFuse S™ Interbody Fusion System," Surgical Technique Manual, MS 4043-02 Rev. O, accessed at http://www.vti-spine.com/docs/Technical%20Documents/InterFuse%20S%20Surgical%20Technique%20-%20International%20Version.pdf, accessed on Sep. 20, 2014, pp. 1-17.

"Interspinous," accessed at https://web.archive.org/web/20131123025814/http://www.thespinemarketgroup.com/p/interspinous-devices.html, accessed on Sep. 20, 2014, pp. 1-12.

"Prodisc-C Nova. Cervical disc prosthesis to restore disc height and maintain segmental motion," Technique Guide, 036.000.568— Synthes, accessed at http://www.synthes.com/MediaBin/International%20DATA/036.000.568.pdf, accessed on Sep. 20, 2014, pp. 1-30.

"Spinal Conditions Treated," accessed at http://www.precisionhealth.com.au/services/pain-management/conditions-treated/spinal-conditions, accessed on Feb. 4, 2015, pp. 1-4.

"The coflex® Interlaminar Implant and the the coflex-F® Interlaminar Stabilization System," accessed at https://web.archive.org/web/20130624072256/http://spinerevolution.com/coflex/, accessed on Feb. 3, 2015, pp. 3.

"X-spine announces FDA clearance of zygafix™ Facet Fusion System," accessed at https://web.archive.org/web/20131214104309/http://x-spine.com/x-spine-announces-fda-clearance-of-zygafix-facet-fusion-system/, May 8, 2013, p. 1.

Barad, J., "Lanx Adds New Device to Their Aspen Line for L5-S1 Fusion," accessed at https://web.archive.org/web/20121219073833/http://www.medgadget.com/2011/09/lanx-adds-new-device-to-their-aspen-line-for-l5-s1-fusion.html, Sep. 30, 2011, pp. 1-3.

Braun, B., "Posterior Thoracolumbar Stabilization System Surgical Technique," accessed at https://web.archive.org/web/20150204090014/http://www.bbraun.no/documents/Products/S4_Posterior_Thoracolumbar_Stabilization_System_Surgical_Technique_09.09.pdf, accessed on Feb. 4, 2015, pp. 44.

Davis, W., et al., "Modern spinal instrumentation. Part 1: Normal spinal implants," Clinical Radiology, vol. 68, No. 1, pp. 64-74 (Jan. 2013).

Eglin, D., and Alini, M., "Degradable Polymeric Materials for Osteosynthesis: Tutorial," European Cells and Materials, vol. 16, pp. 80-91 (Dec. 19, 2008).

Eisner, W., "Lanx's aspen system achieves 94% fusion rate," accessed at http://ryortho.com/breaking/lanx039s-aspen-system-achieves-94-fusion-rate/, Sep. 19, 2012, pp. 1-2.

International Search Report and Written Opinion for International Application No. PCT/IB2014/000773, mailed on Sep. 8, 2014.

International Search Report and Written Opinion for International Application No. PCT/US2013/000984, mailed on Oct. 24, 2013.

Kettler, A., et al., "Are the spines of calf, pig and sheep suitable models for pre-clinical implant tests?" Eur Spine J., vol. 16, No. 12, pp. 2186-2192 (Dec. 2007).

Li, H., et al., "Effects of Pore Morphology and Bone Ingrowth on Mechanical Properties of Microporous Titanium as an Orthopaedic Implant Material," Materials Transactions, vol. 45, No. 4, pp. 1124-1131 (2004).

Mano, J. F., et al. "Bioinert, biodegradable and injectable polymeric matrix composites for hard tissue replacement: state of the art and recent developments," Composites Science and Technology, vol. 64, Issue 6, pp. 789-817 (2004).

Moreland, D.B., et al., "Anterior cervical discectomy and fusion with implantable titanium cage: initial impressions, patient outcomes and comparison to fusion with allograft," The Spine Journal, vol. 4, No. 2, pp. 184-191 (Mar.-Apr. 2004).

Panjabi, M. M., et al., "Human Lumbar Vertebrae Quantitative Three-Dimensional Anatomy," SPINE, vol. 17, No. 3, pp. 299-306 (Mar. 1992).

Smit, T. H., "The use of a quadruped as an in vivo model for the study of the spine—biomechanical considerations," Eur Spine J, vol. 11, No. 2, pp. 137-144 (Apr. 2002).

Wilke, H.-J., et al., "Biomechanical Comparison of Calf and Human Spines," Journal of Orthopedic Research, vol. 14, No. 3, pp. 500-503 (May 1996).

Supplementary European Search Report dated Jun. 10, 2016 as received in Application No. 13833180.6.

"Precision Spine & Pain Clinic: Overview of Spinal Anatomy," accessed at https://web.archive.org/web/20111224213425/http://www.precisionspine.com.au/html/conditions_overview.html, accessed on Mar. 17, 2017, pp. 2.

Extended European Search Report for European Application No. 14839020.6 dated Apr. 18, 2016, pp. 7.

\* cited by examiner

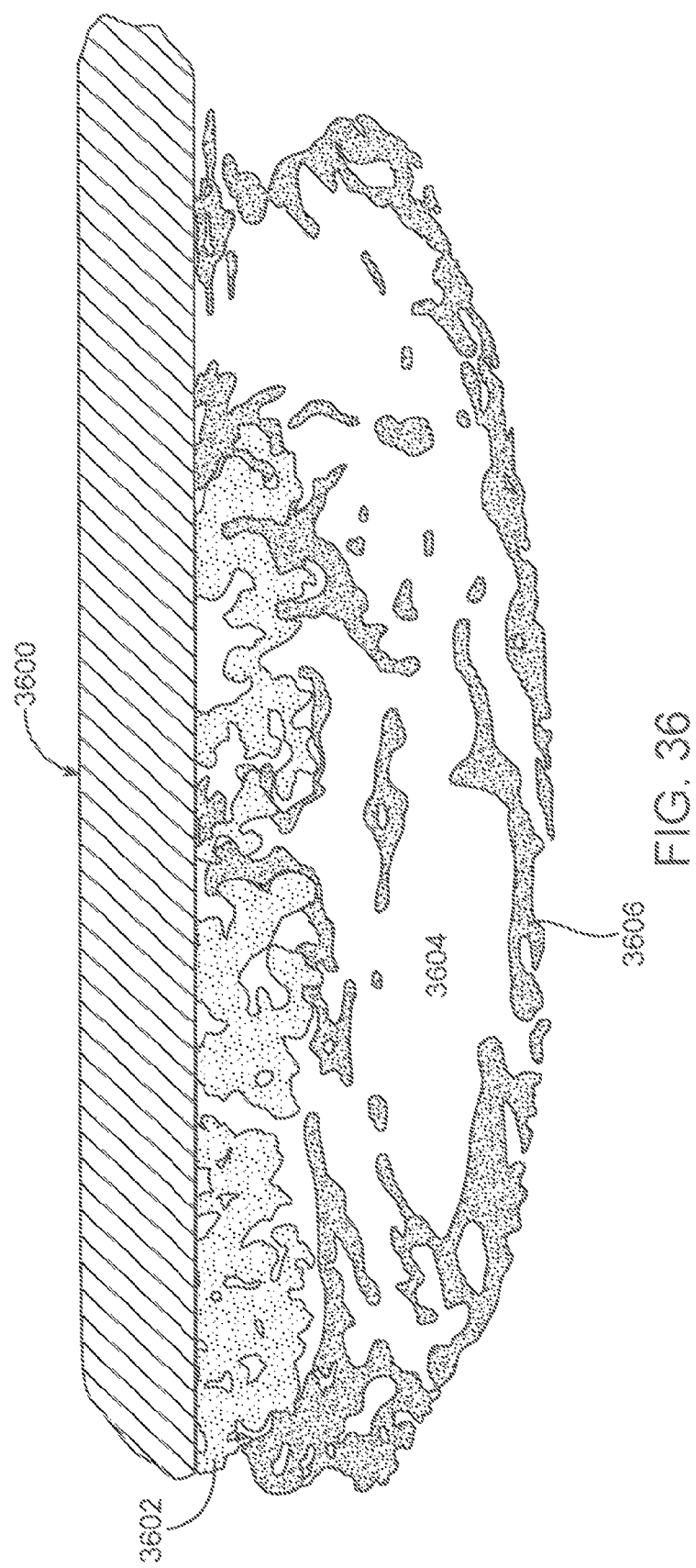

BONE STABILIZATION DEVICE AND METHODS OF USE

CROSS-REFERENCE TO RELATED APPLICATION

The present application is a U.S. National Stage filing under 35 U.S.C. § 371 of International Application No. PCT/AU2013/000984, filed on Aug. 30, 2013.

TECHNICAL FIELD

The present disclosure relates to a medical implant for stabilizing bones, for example, adjacent bones such as vertebrae, and a method of sugically stabilizing bones.

BACKGROUND

Unless otherwise indicated herein, the materials described in this section are not prior art to the claims in this application and are not admitted to be prior art by inclusion in this section.

Surgical techniques are often necessary to treat spinal disorders. Spinal fusion is one such technique and generally indicated in circumstances where the spine is incapable of correctly performing key functions or through deterioration or misalignment impinges on related nerves. Spinal fusion often involves use of artificial synthetic implants that are surgically positioned to bridge between and stabilize adjacent vertebrae. Such implants often require the use of screws or other fasteners to ensure ongoing stability and provide a stable mechanical environment to allow bone formation as opposed to fibrous or soft tissue, which does not provide the sufficient mechanical properties to stabilize the site.

SUMMARY

Described herein are devices and methods for providing bone stabilization or bone fusion by using a bone stabilization or bone fusion device without the need for a fastener to attach the device to the bone. The devices and methods are generally determined by a determined rigidity factor described herein.

In an embodiment, there is described a bone fusion device. The bone fusion device has a body a first end adapted for resting on a first bone. The first end generally has a bone engagement feature. The device has a second end adapted for resting on a second bone. There is a bridge portion connecting the first end and the second end. Generally, at least a portion of the bridge can be positioned between the first bone and the second bone when the device is in use. The bridge portion generally has a rigidity of about $5.5 \times 10^{-4}$ $Nm^2$ or higher.

In an embodiment, there is a method of achieving an increase in stability of two or more bones relative to each other. The method involves selecting a stabilizer device having suitable dimensions and mechanical parameters to achieve a desired increase in stability, implanting the stabilizer device at a location relative to the two or more bones and allowing fusion or restriction of motion of the stabilizer device to the two or more bones. Generally, the fusion occurs through bone integration with the stabilizer device within a defined period. Generally, the fusion occurs with decortication of the bone area where the stabilization is placed, but without the use of a bone osteogenesis material such as an autograft, allograft or synthetic material.

In an embodiment, there is a bone graft substitute. The bone graft substitute has a body with a first end adapted to rest on a first bone. The first end has a bone engagement feature. The bone graft substitute has a second end adapted to rest on a second bone. There is a bridge portion connecting the first end and the second end. The bridge portion can be positioned between the first bone and the second bone when the bone graft substitute is in use. The bone engagement feature is configured for fusion with a damaged bone surface absent bone graft material.

In another embodiment, there is a bone fusion device with a body. The body has a first end adapted to rest on a first bone. The first end has a bone engagement feature. There is a second end adapted to rest on a second bone. The second end has a bone engagement feature. There is a bridge portion that connects the first end and the second end. The bridge portion can be positioned between the first bone and the second bone when the device is in use. The body is adapted to withstand relative movement of the body when the first and second ends become fused to the first and second bones.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 36 is a sectioned lateral of an embodiment illustrating bone ingrowth on the bone stabilizer device;

DETAILED DESCRIPTION

Figure 1:
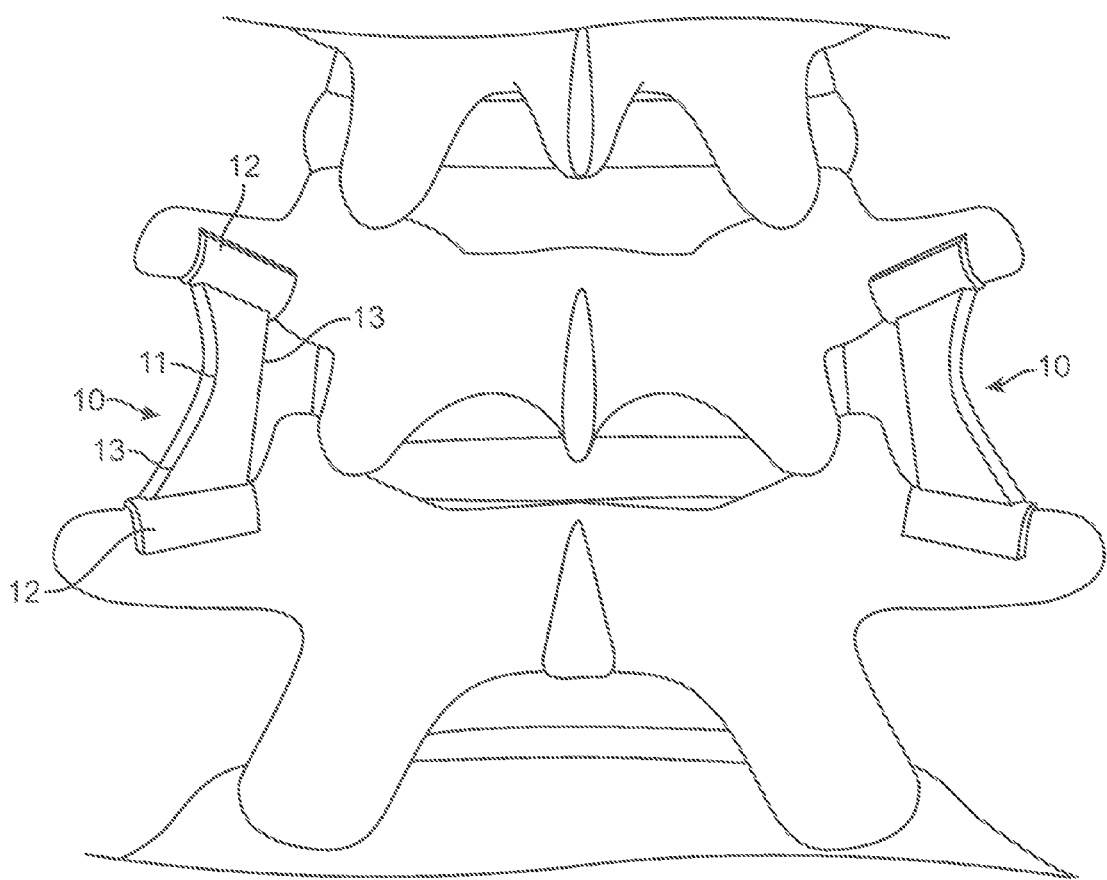
FIG. 1 is a view of an embodiment of a bone stabilizer device.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Described herein are devices and methods for providing bone stabilization or bone fusion by using a bone stabilization or bone fusion device without the need for a fastener to attach the device to the bone.

Briefly stated, technologies are generally provided for devices and methods for use in bone fixation, bone fusion and/or bone stabilization. In various embodiments, the devices and methods relate to a bone stabilization having a first end, second end and a bridge connecting the first and second ends. The first end has a bone engagement feature and may be fused to the bone over time without the use of osteogenic materials.

According to an embodiment, there is provided a bone fusion device with a body having a first end, a second end and a bridge between the first and second end. The first end is adapted to rest on a first bone and may have a bone engagement feature. The second end is adapted to rest on a second bone. The bridge portion connects the first end and the second end. At least a portion of the bridge portion may be positioned between the first bone and the second bone when the device is in use. The bridge portion has a rigidity of about $5.7 \times 10^{-4}$ $Nm^2$ or higher.

In an embodiment, the body may consist at least partially of titanium. In other arrangements, the body may comprise one or more biocompatible polymers, which may or may not also be used in conjunction with a biocompatible metal, such as titanium.

In an embodiment, a bone engagement feature may be on the first end and the second end. In another embodiment, the first end and the second end may have a bone integration feature. The bone integration feature may be a fastener. In some embodiments, the bone integration feature may be adapted to trigger an osteogenic response in a bone. The bone engagement feature as used herein refers to a modified surface area to rest on the bone. The bone engagement feature may be a textured surface with etching, pores or other features providing a roughened surface for bone growth to engage the stabilization device. Bone integration refers to a mechanical feature to pierce at least the surface of the bone and cause an injury to the bone sufficient to trigger a bone healing response. The bone integration feature may provide mechanical connection between the bone stabilizer device and the bone; however, mechanical engagement is not its primary purpose.

In an embodiment, the bridge may have a lower aspect ratio (W:H) than the first end. Alternatively, the bridge may also have a lower aspect ratio than the second end. The bridge may be narrower than either or both of the first and second ends with respect to an axis of the device between the first end and the second end. In an embodiment, the bridge may be located toward a side of the device. Alternatively, the bridge may be located centrally with respect to the axis of the device between the first end and the second end. In still another embodiment, the bridge may include a first portion and a second portion, wherein the first portion is relatively thicker than the second portion. Alternatively, the body may be substantially flat.

The bone engagement feature may be capable of receiving bone ingrowth, ongrowth and/or through growth.

In an embodiment, the body may be made of a single material. In some embodiments, the body may be made of two or more different materials. The two or more different materials may be selected from: a polymer; a metal; and an alloy material. The two or more different materials may include a first polymer and a second polymer. The first and second polymers may be chosen from a group comprising: PEEK; and modified PEEK. The body may comprise two or more layers of different materials. Other materials are contemplated, and are discussed in detail below.

In some embodiments, the body may comprise a reinforcement element. The reinforcement element may comprise biocompatible metal or metal alloy and the bridge portion may comprise a polymer.

In some embodiments, the bone stabilization device may be configured for use in conjunction with a biochemical and/or biological agent for the stimulation of bone growth. However, the use of such an agent may not be necessary for the device to fuse successfully to bone.

In an embodiment, the bone engagement feature may comprise a textured surface, or a plurality of perforations. The textured surface may comprise one or more of a porous surface, a roughened surface and/or a sintered surface.

In an embodiment, the device may be configured such that the first and second bones are vertebral components. The vertebral components may be selected from one or more of: vertebral bodies; spinous processes; facet joints; transverse processes. If the vertebral components are transverse processes, the device may be adapted for use where the transverse processes are adjacent each other. In another embodiment, the first and second bones may be any two adjacent bones in the hand or foot. Further, the first and second bones may be two pieces of a normally single bone. For example, the normally single bone may have been fractured through trauma, or severed as part of a procedure.

In an embodiment, the edge of the elongate body may have a thickness of about 0.2-5 mm, alternatively about 0.5-3.5 mm, further alternatively about 1-3.5 mm and further alternatively about 1-2 mm.

In an embodiment, the bridge portion may comprise a bone engagement portion on at least a portion thereof.

According to an embodiment, there is provided a bone graft substitute comprising the bone fusion device described above, including any one or more of the above described features.

According to an embodiment, there is provided a bone graft substitute that includes a body, the body including a first end adapted for resting on a first bone, the first end having a bone engagement feature; a second end adapted for resting on a second bone; and a bridge portion connecting the first end and the second end, the bridge portion adapted to be positioned between the first bone and the second bone in use. The bone engagement feature is configured for fusion with a damaged bone surface absent bone graft material. The bone graft substitute of this embodiment may incorporate any one or more of the features of the bone fusion device described above.

According to another embodiment, there is provided a bone fusion device that includes a body, where the body includes a first end adapted for resting on a first bone, the first end having a bone engagement feature; a second end adapted for resting on a second bone, the second end having a bone engagement feature; and a bridge portion connecting the first end and the second end, the bridge portion adapted to be positioned between the first bone and the second bone in use. The body is adapted to withstand relative movement between the first and second bones when the first and second ends become fused on or with the first and second bones.

In an embodiment, the relative movement may comprise one or more of flexion, extension, lateral bending and torsional movement. The device may be configured to withstand, in use, brittle failure and plastic deformation during such movement. Any one of the above described bone fusion devices and bone graft substitutes may embody any one or more of the features described above with respect to other embodiments of bone fusion devices or bone graft substitutes.

According to an embodiment, there is provided a method of achieving an increase in stability of two or more bones relative to each other, where the method includes selecting a stabilizer device having suitable dimensions and mechanical parameters to achieve the increase in stability; implanting the stabilizer device at a location relative to the two or more bones; and allowing fusion or restriction of motion of the stabilizer device to the two or more bones. Fusion occurs through bone integration with the stabilizer device within a defined period.

In other embodiments, the method is used to stabilize or fuse the spine of a patient. In this embodiment, the stabilizer can be implanted between the vertebrae, for example, the spinous processes, of adjacent vertebrae or the body of the vertebrae. The stabilizer device can extend over a single level between adjacent vertebrae or over multiple levels of three or more vertebrae. The method can be used to stabilize the cervical, thoracic and lumbar regions of the spine. The method can also direct and/or control the growth of one side of the spine, for example, in the case of abnormal curvatures of the spine (scoliosis). Other suitable locations can be envisaged including craniofacial, dental and trauma applications.

In some embodiments, the stabilizer device may be used as a treatment system for the spine from the cervical to sacrum.

In some embodiments, selection of the stabilizer device can involve selecting a stabilizer device having a particular geometry and/or mechanical properties from a range of stabilizer devices having a range of geometries and/or mechanical properties. The mechanical properties can include devices having varying measures of rigidity that can be controlled through the Young's modulus (E), which can be determined by the material used and/or geometry of the device. The material and/or geometry used dictates the distribution of mass of the device (I, moment of inertia) and when multiplied together equals the rigidity (Rigidity=E×I). This ability to select a stabilizer device provides the surgical team entrusted with performing the fusion or stabilization of, for example the spine, with a range of options that ensures the best possible stabilizer device is used in light of factors such as one or more of the patient's anatomy, size, age, condition and requirements. In one embodiment, the same implant can be used on the right and left side of the spine. In another embodiment, different implants can be used on the right and left sides and/or at different levels depending on the biomechanical and anatomical requirements.

The step of implanting the stabilizer device can comprise an extraosseous implantation. By extraosseous, it is to be understood that the implantation step need not require fixation of the device to the pedicle of the spine through the use of screws, bolts or other fasteners. However, fixation using such devices can be used if desired.

The step of fusing the selected stabilizer to the bone can comprise biological fixation.

In one embodiment, the region of the bone that is desired to fuse or stabilize with the respective bone integration portions can undergo decortication. The process of decortication can comprise the surgical team using a high-speed burr to remove a layer of outer bone from the transverse processes. This allows access to the bone marrow to facilitate bone ingrowth as well as a possible means of a geometrically created pocket or gutter for the implant to be placed for initial stability.

In another aspect, there is disclosed a bone stabilizer device for use in the method as defined herein.

The bone stabilizer device in this aspect can have one, some or all of the features of the bone stabilizer device as defined herein with regard to the other aspects.

In still another aspect, there is disclosed a bone stabilizer device comprising a main body having a first end and a second end, at least a portion of the device at or adjacent the first end and/or the second end comprising a bone integration or engagement portion.

In this aspect, each bone integration portion can be adapted to allow bone integration therein or thereon within the defined period. In one embodiment, stabilization can occur within 4-8 weeks of implantation due to ingrowth or ongrowth of autogenous tissues.

In another embodiment, the bone stabilizer device can have one or more of the bone engagement portions engaged around the bones to be stabilized. For example, a bone engagement portion can be deformable by the surgeon and so folded or engaged with the bone ends so as to capture the relevant bones. In a still further embodiment, the main body of the stabilizer can be deformable. The provisions of deformable bone engagement portions and/or a deformable main body can also result in a tensile or compressive load between the bone segments as result of the fixation or be performed in a neutral loading aspect. The deformable ability of the bone segment portions and/or the main body can also be used to re-align or reduce any anatomical features that need to be corrected by the surgeon at the time of the surgical procedure.

In an embodiment, the bone stabilizer device can be formed from a suitable biocompatible material including a metal, a metal alloy or polymeric material or combination thereof. The device can also comprise an allograft material. The device can be formed in one piece and alone span the distance between adjacent transverse processes. The stabilizer device can be, at least at the time of implantation, a solid one piece member formed of a single material suitable for the purpose of spinal fusion.

In one embodiment, the device can be formed from titanium or a titanium alloy. Other suitable metals include stainless steel, cobalt-chromium alloys, and tantalum. In another embodiment, the device can be formed from a suitable polymer including non-degradable polymers, such as PEEK and PE as well as modified versions of these materials (for example, PEEK+calcium phosphates and PE+vitamin E, or metal coatings or surface texturing).

The bone integration portions can comprise a three-dimensional space to allow bone integration into and/or onto the portions. The three dimensional space can be provided by a three-dimensional substrate, for example beads, and/or by the provision of holes through the bone integration portions. Other methods for achieving bone integration can include the provision of an appropriate surface topography, for example a roughened or textured area and/or by the provision of osteoconductive coatings, such as calcium phosphates.

In a further embodiment, the main body of the device can also comprise a three-dimensional space to allow bone integration into and/or onto the main body. The three dimensional space can be provided by a three-dimensional substrate, for example beads, and/or by the provision of holes through the main body. Other methods for achieving bone integration can include the provision of an appropriate surface topography, for example a roughened or textured area and/or by the provision of osteoconductive coatings, such as calcium phosphates onto the main body. In this regard, the device itself can provide a metal and/or polymeric scaffold for tissue integration to be achieved through the device.

The integration of bone ingrowth or ongrowth to the device at the bone implant interface provides a biological stabilization while initial fixation can be achieved through the use of various fixation techniques including suture, screws, staples or the geometry of the device alone through dimensions or by deforming the said geometry at the time of implant to provide a close approximation to the bone bed.

Various examples of bone stabilizer devices are depicted in the drawings. It will be appreciated that the drawings only depict some of the various geometries and designs that can comprise the bone stabilizer device.

The depicted bone stabilizer devices, either in the form of bone fusion devices, or bone graft substitutes, can be used to achieve an increase in stability of two or more bones relative to each other, for example adjacent vertebrae. The increase in stability can be achieved by: selecting a stabilizer device having suitable dimensions and mechanical parameters to achieve the increase in stability; implanting the stabilizer device at a location relative to the two or more bones; and allowing fusion or restriction of motion of the stabilizer device to the two or more bones.

Using this method and the selected stabilizer device, fusion can occur through bone integration with the stabilizer device within a defined period.

As described, the method and/or device can be used to stabilize or fuse the spine of a patient. Where used for this application, the stabilizer device can be implanted between the vertebrae, for example, the spinous processes, of adjacent vertebrae or the body of the vertebrae. The stabilizer device can extend over a single level between adjacent vertebrae (as depicted in the figures) or over multiple levels of three or more vertebrae. The method and/or device can be used to stabilize the cervical, thoracic and lumbar regions of the spine. The method and/or device can also direct and/or control the growth of one side of the spine, for example, in the case of abnormal curvatures of the spine (scoliosis). Other suitable locations can be envisioned including craniofacial, dental and trauma applications.

In the method, the step of selecting a stabilizer device can comprise selecting a stabilizer device having a particular geometry and/or mechanical properties from a range of stabilizer devices having a range of geometries and/or mechanical properties. Examples of stabilizer devices having different geometries are provided in the drawings. The mechanical properties can include devices having varying measures of rigidity, which can be controlled through the Young's modulus (E) which can be determined by the material used and/or geometry of the device. The material and/or geometry used dictates the distribution of mass of the device (I, moment of inertia) and when multiplied together equals the rigidity (Rigidity=E×I). This ability to select a stabilizer device provides the surgical team entrusted with performing the fusion or stabilization, of for example the spine, with a range of options that ensures the best possible stabilizer device is used in light of factors such as one or more of the patient's anatomy, size, age, condition and requirements.

As depicted in some embodiments, the same implant can be used on the right and left side of the spine. It will be appreciated that different implants can be used on the right and left sides and/or different levels depending on the biomechanical and anatomical requirements.

The step of implanting the stabilizer device into the locations as depicted in the figures can comprise an extraosseous implantation. By extraosseous, it is to be understood that the implantation step need not require fixation of the device to the pedicle of the spine, or elsewhere on the spine, through the use of screws, bolts or other fasteners. However, fixation using such devices can be used if desired.

In the method, the step of fusing the selected stabilizer device to the bone can comprise biological fixation.

The region of bone that is desired to fuse or stabilize with the respective bone integration portions can undergo decortication. The process of decortication can comprise the surgical team using a high-speed burr to remove a layer of outer bone from the transverse processes. This allows access to the bone marrow to facilitate bone ingrowth as well as a possible means of a geometrically created pocket or gutter for the implant to be placed for initial stability.

Various embodiments of a bone stabilization device, bone fusion device, or bone graft substitute are now described. In an embodiment, there is a bone fusion device having a body, which may be elongate. The body has a first end for resting on a first bone and a bone engagement feature.

There is a second end adapted for resting on a second bone. A bridge portion connects the first end and the second end. The bridge portion can be positioned between the first bone and the second bone when the device is in use. The body has a minimum rigidity of about $5.7 \times 10^{-4}$ Nm$^2$.

In one aspect of the device, the rigidity feature is on the body. In another aspect, the rigidity feature is on the bridge.

In an embodiment, the body may be partially or entirely made of a metal or metal alloy. Examples of such metals are titanium, tantalum, stainless steel, chromium or any alloys using those metals. The device may be made of any polymer material herein described, and may be made of a sandwich of two or more materials including all metals, all alloys, all polymers or all other biocompatible materials. The device may be made from two or more material described herein in a non-layer arrangement.

In an embodiment, the body is substantially flat. In another embodiment, the body may have an aspect ratio (relation of Width to Height W:H) that is less than the aspect ratio of either the first end, the second end or the average of the first and second end. In various aspects, the device may have a body with a length of about 1-4 mm for working with small bones or bones with small gaps between them (e.g., broken bones or the small bones of the feet, hands or inner ear). In another aspect, the elongate body may be several centimeters (cm) long, such as for bridging the span of two transverse processes (spine), opposing end of the pubic bridge (pelvis) or gap between ribs. In various embodiments, the width and height of the bridge portion may be slightly lower in height, or slightly narrower in width. In other aspects, the average area defined by the perimeter of the width contours of the bridge portion may be mathematically determined and compared to the absolute area defined by the distance (length) between the first end and the second end and the average width of the first and second end. The calculated actual width and the absolute width (and similarly for their height values) may be used for determination of aspect ratios when the borders of the bridge portion are irregular.

In still another embodiment, the second end may have a bone engagement feature. In some embodiments, the bone engagement feature is designed to rest on the bone without actively binding, engaging or fastening to the bone. In some embodiments, the device may have a bone integration feature, which may include one or more fasteners such as spikes, screws, pins, clamps or the like. The bone integration feature may pierce the outer layer of the bone and cause osteogenesis. The bone engagement feature may receive ingrowth, ongrowth or through growth.

In various embodiments, the determination of rigidity and of specific dimensions of the spinal stabilizer device are provided for in close estimates and/or close calculations. Due to variability in the purity of materials and/or variations in the shape (geometry) and machining or crafting capability of producing the stabilizer device described herein, the term "about" is used to provide for some margin of close approximation. Some examples may call for dimensions of about 0.5 mm to 3 mm thickness or edge without specifying tolerance. In these kinds of measurements and all rigidity calculations, the terms are generally close to those presented but may vary up and down slightly due to imprecision in calculation, manufacturing technique and/or machining process. Where a conscious design choice is made to modify the parameters of physical dimensions or performance to a specification close to those described herein, and achieve the same level of performance intended, the equivalent structure is also intended to be "about" the same as those provided herein.

The rigidity may be determined using various calculations considering the combination of material used and shape (geometry) of the device. Two examples are provided here in tables 1 and 2.

|  | Stiffness max | 10% min | of total load |
|---|---|---|---|
| lumbar | | | |
| torque | 10 | 1 | Nm |
| moment arm | 0.05 | 0.05 | m |
| load | 200 | 20 | N |
| angular deflection | 0.000 | 2.727 | rad |
| angular deflection | 0.010 | 156.261 | degrees |
| cervical | | | |
| torque | 2.5 | 0.25 | Nm |
| moment arm | 0.04 | 0.04 | m |
| load | 62.5 | 6.25 | N |
| angular deflection | 0.000 | 0.545 | rad |
| angular deflection | 0.002 | 31.252 | degrees |
| thoracic | | | |
| torque | 7.5 | 0.75 | Nm |
| moment arm | 0.045 | 0.045 | m |
| load | 166.667 | 16.667 | N |
| angular deflection | 0.000 | 1.841 | rad |
| angular deflection | 0.00042 | 105.476 | degrees |

Table 1 provides calculations of torque, moment arm, load and angular deflection for devices selected for use in three areas of the spine, and made of medical grade titanium.

|  | max | 10% min | of total load |
|---|---|---|---|
| lumbar | | | |
| torque | 10 | 1 | Nm |
| moment arm | 0.05 | 0.05 | m |
| load | 200 | 20 | N |
| angular deflection | 0.005 | 5.208 | rad |
| angular deflection | 0.306 | 298.416 | degrees |
| cervical | | | |
| torque | 2.5 | 0.25 | Nm |
| moment arm | 0.04 | 0.04 | m |
| load | 62.5 | 6.25 | N |
| angular deflection | 0.001 | 3.292 | rad |
| angular deflection | 0.061 | 188.628 | degrees |
| thoracic | | | |
| torque | 7.5 | 0.75 | Nm |
| moment arm | 0.045 | 0.045 | m |
| load | 166.666667 | 16.66666667 | N |
| angular deflection | 0.000 | 3.516 | rad |
| angular deflection | 0.01289 | 201.430 | degrees |

Table 2 provides calculations for a device for placement in three areas of the spine and determine torque, moment arm, load and angular deflection for PEEK.

As already described, various examples of bone stabilizer devices are depicted in the figures. One example is depicted generally as 10 in FIGS. 1 and 2. The stabilizer device 10 comprises a flat-plate main body 11 that is constructed such that one implantation is oriented in the coronal plane. The main body 11 has non-parallel side edges 13, with one edge being concave relative to the other. At each end of the main body 11, there is a substantially U-shaped bone engagement member 12. Both of the bone engagement members 12 are adapted to be positioned on or adjacent the spinous processes of adjacent vertebrae.

In the depicted embodiment, both bone engagement members 12 are adapted to allow bone integration therein or thereon within a defined period. In this regard, stabilization can occur within 4-8 weeks of implantation due to ingrowth or ongrowth of autogenous tissues.

Alternative arrangements are provided in FIGS. 3-13. The bone engagement members of the embodiments depicted in FIGS. 3-13 can also be adapted to allow bone integration therein or thereon within a defined period as defined above.

Figure 3:
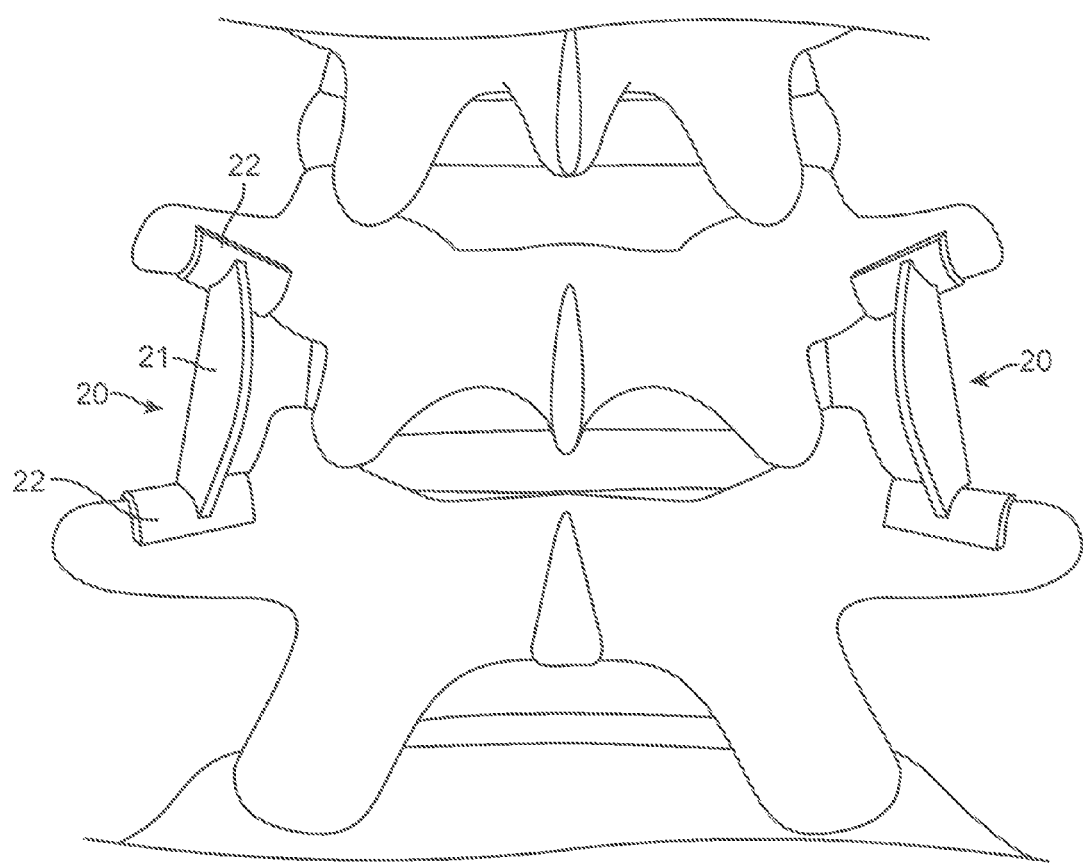
FIG. 3 is a view of an embodiment of a bone stabilizer device.
Figure 4:
FIG. 4 is a lateral view of the implant of FIG. 3.

In FIGS. 3 and 4, the stabilizer device 20 again has a flat plate main body 21 that is constructed such that one implantation is oriented slightly offset from the sagittal plane. The main body 21 again has non-parallel side edges with one edge being convex relative to the other. At each end of the main body 21, there is a substantially U-shaped bone engagement member 22. Both of the bone engagement members 22 are adapted to be positioned on or adjacent the spinous processes of adjacent vertebrae.

Figure 5A:
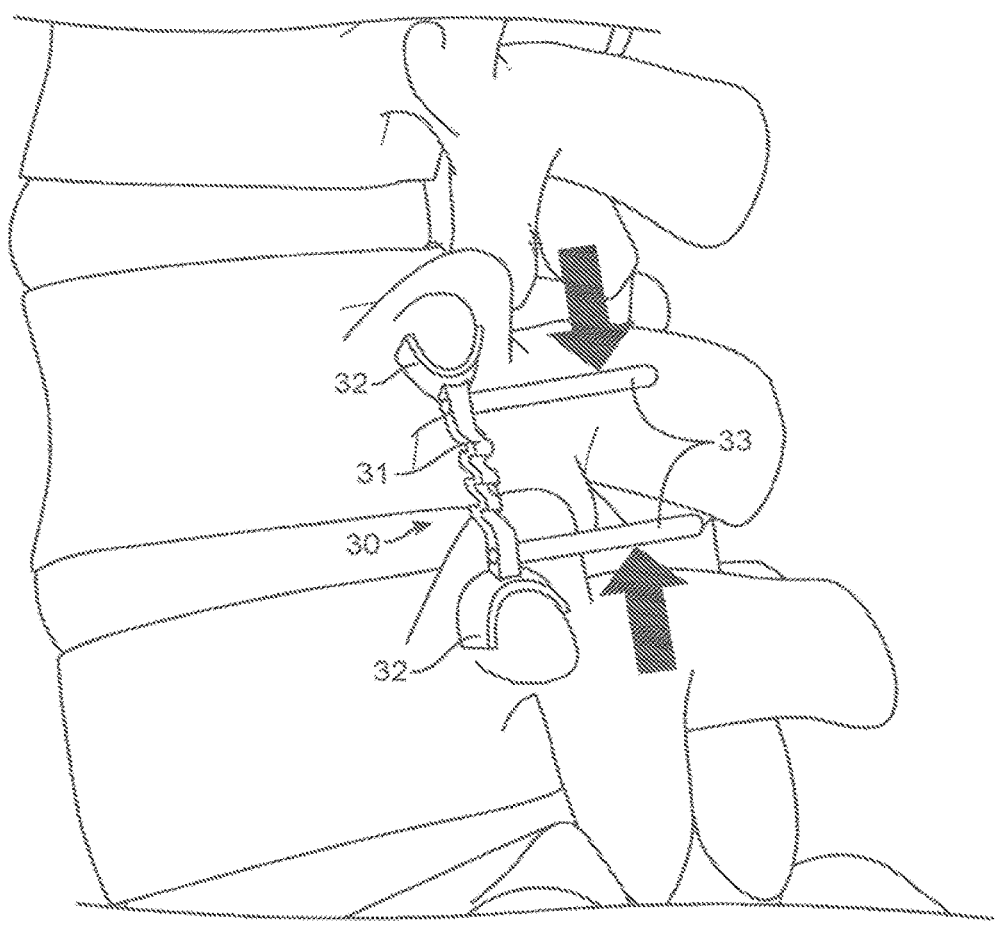
FIG. 5A is a lateral view of an embodiment of a bone stabilizer device having outwardly extending pins.
Figure 5B:
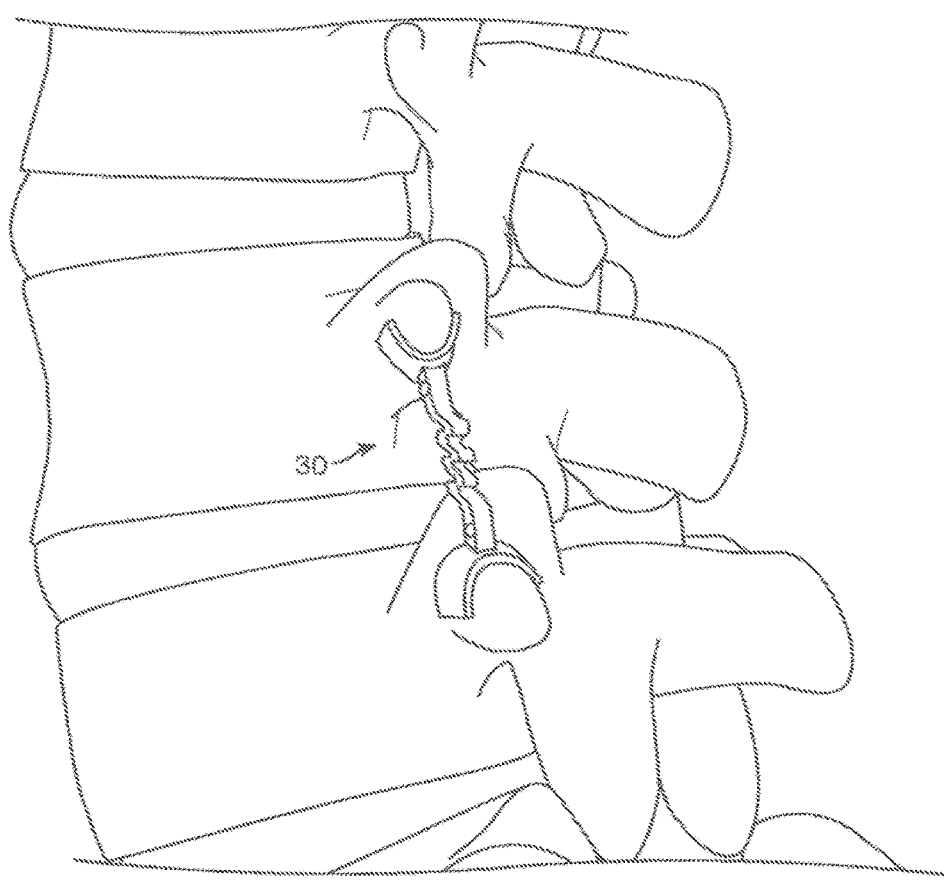
FIG. 5B is a further lateral view of the embodiment of FIG. 5A with the pins released.
Figure 5C:
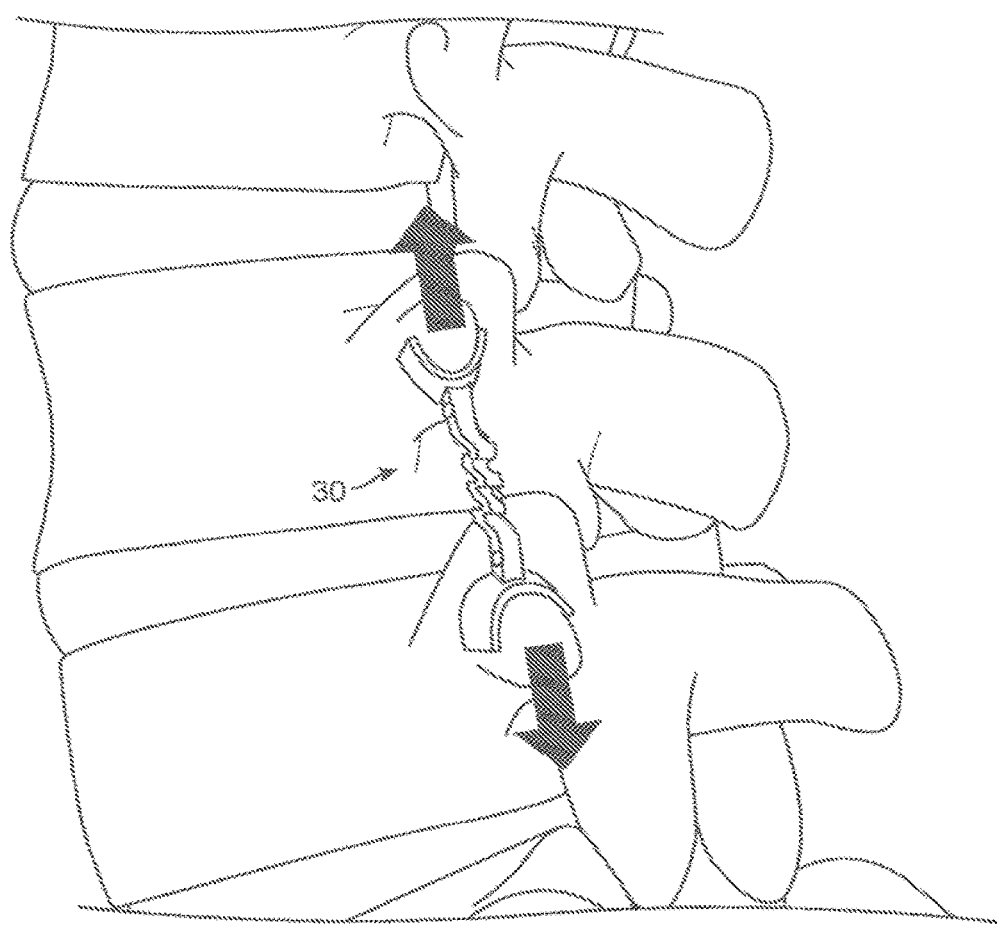
FIG. 5C is a further lateral view of the embodiment of FIGS. 5A and 5B demonstrating how the stabilizer is distracting adjacent vertebrae.

In FIGS. 5A to 5C, a further embodiment of a cone stabilizer device is depicted generally as 30. The device 30 has a spring-form main body 31 with substantially U-shaped cup members 32 provided at each end. The device 30 is provided with pins 33 that serve to compress the main body 31. The pins 33 can be released (see FIG. 5B) so allowing the main body to relatively push against the spinous processes (see FIG. 5C).

Figure 2:
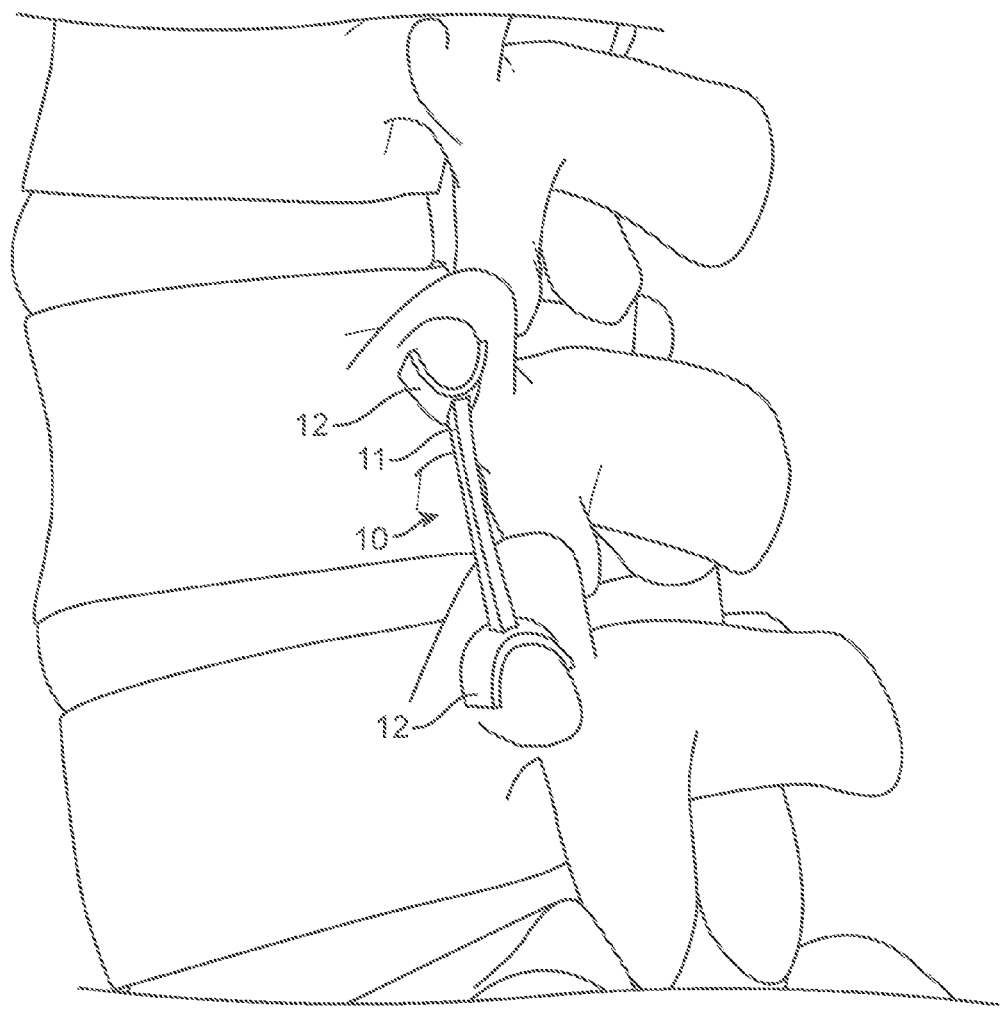
FIG. 2 is a lateral view of the implant in FIG. 1.
Figure 6:
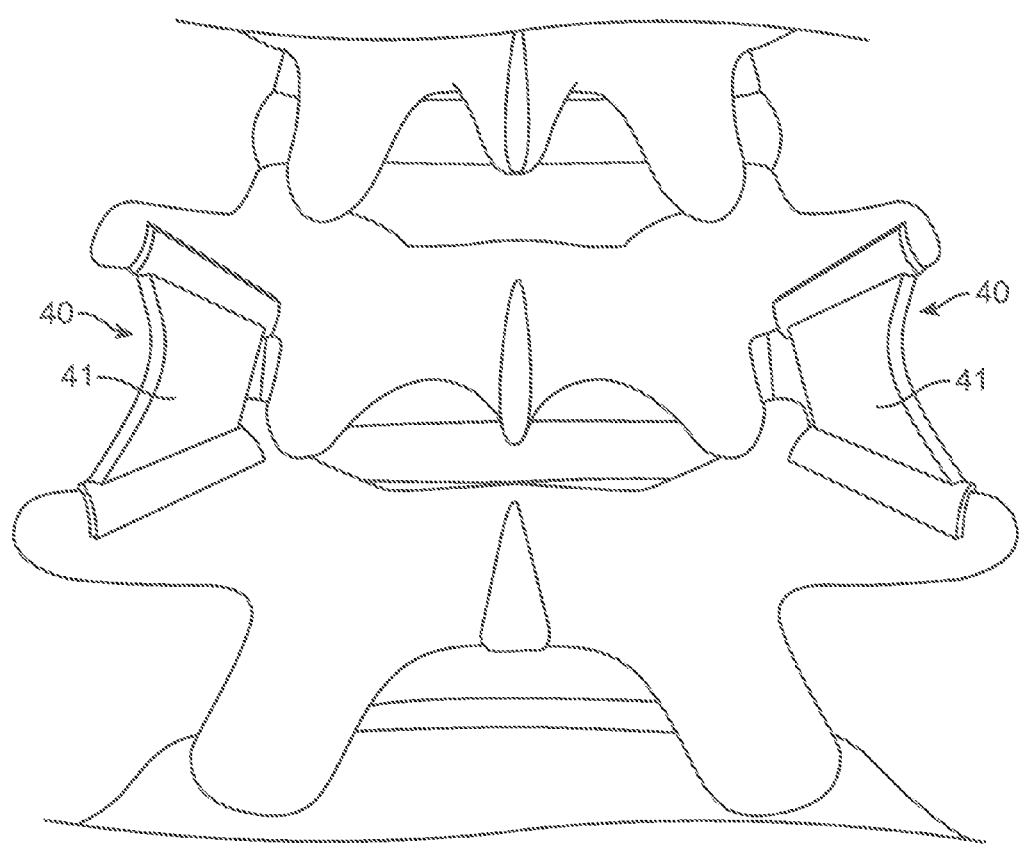
FIG. 6 is a view of an embodiment of a bone stabilizer device.
Figure 7:
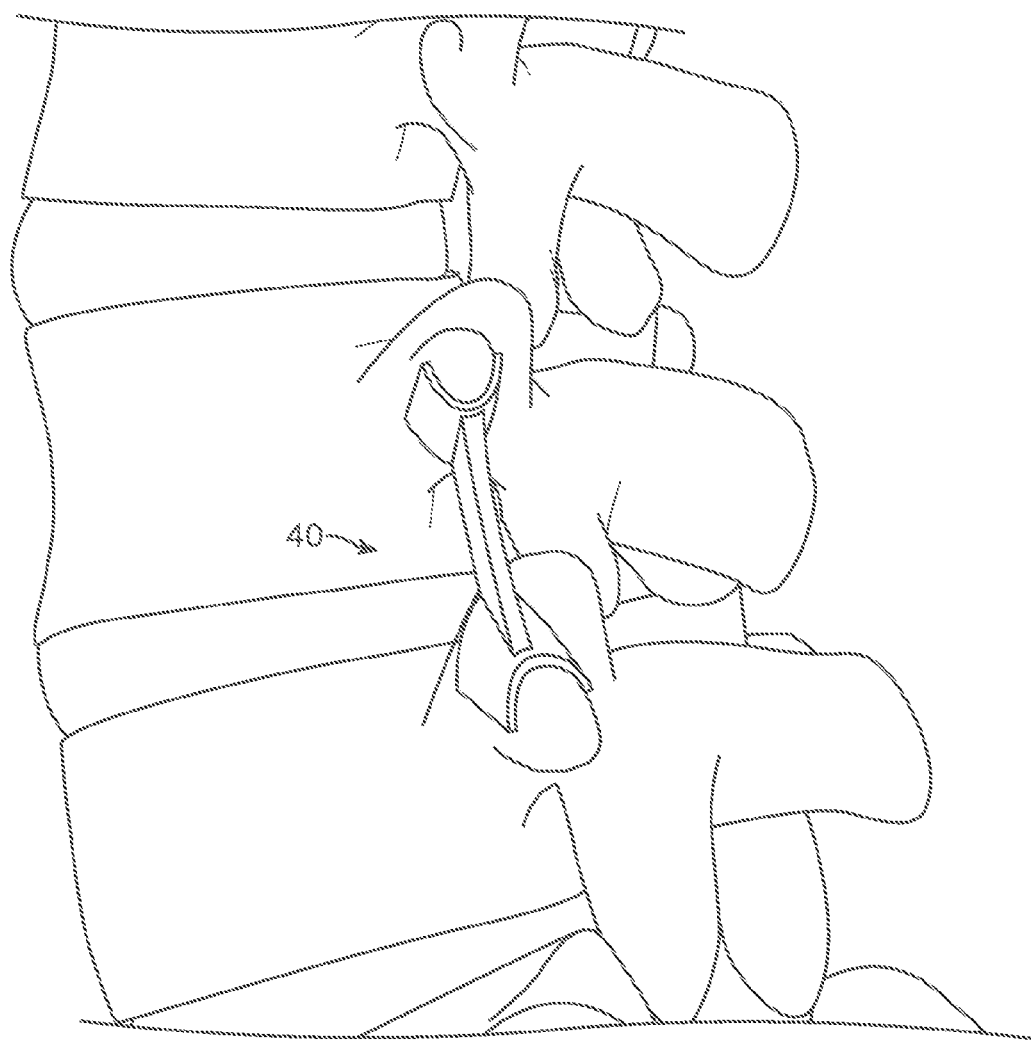
FIG. 7 is a lateral view of the implant of FIG. 6.
Figure 8:
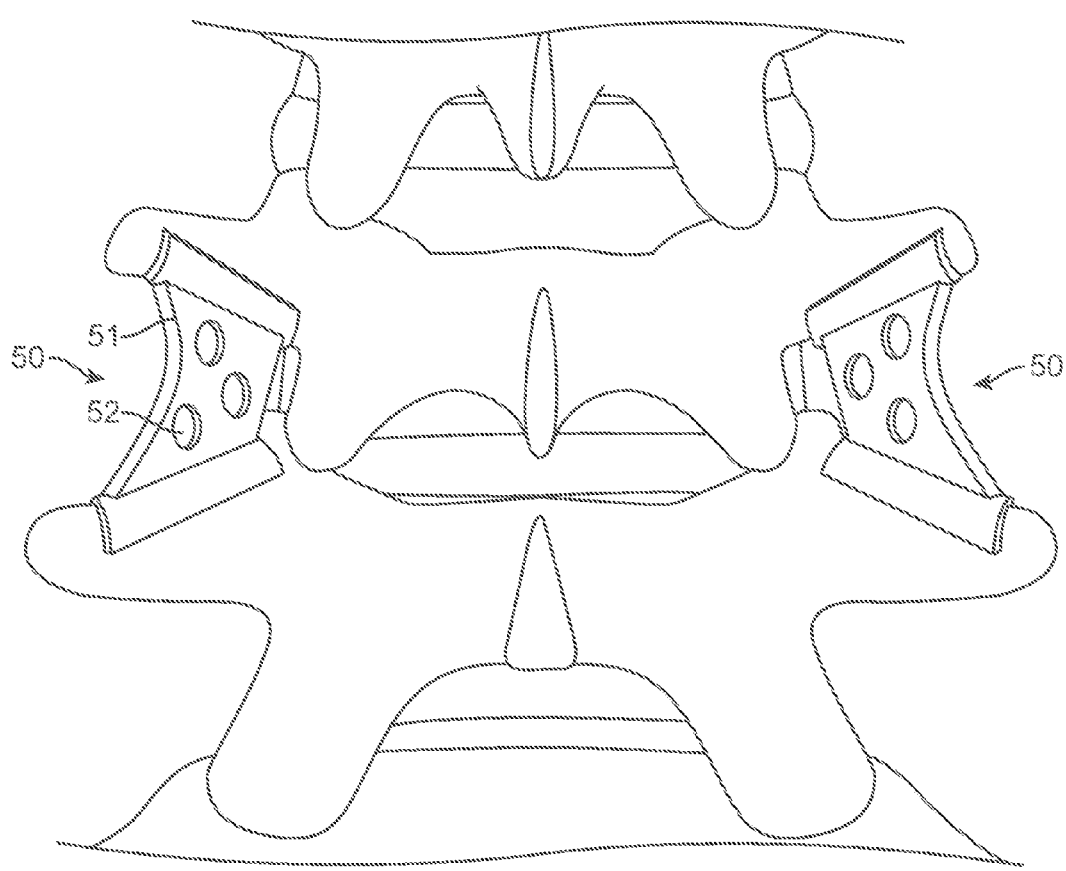
FIG. 8 is a view of an embodiment of a bone stabilizer device.
Figure 9:
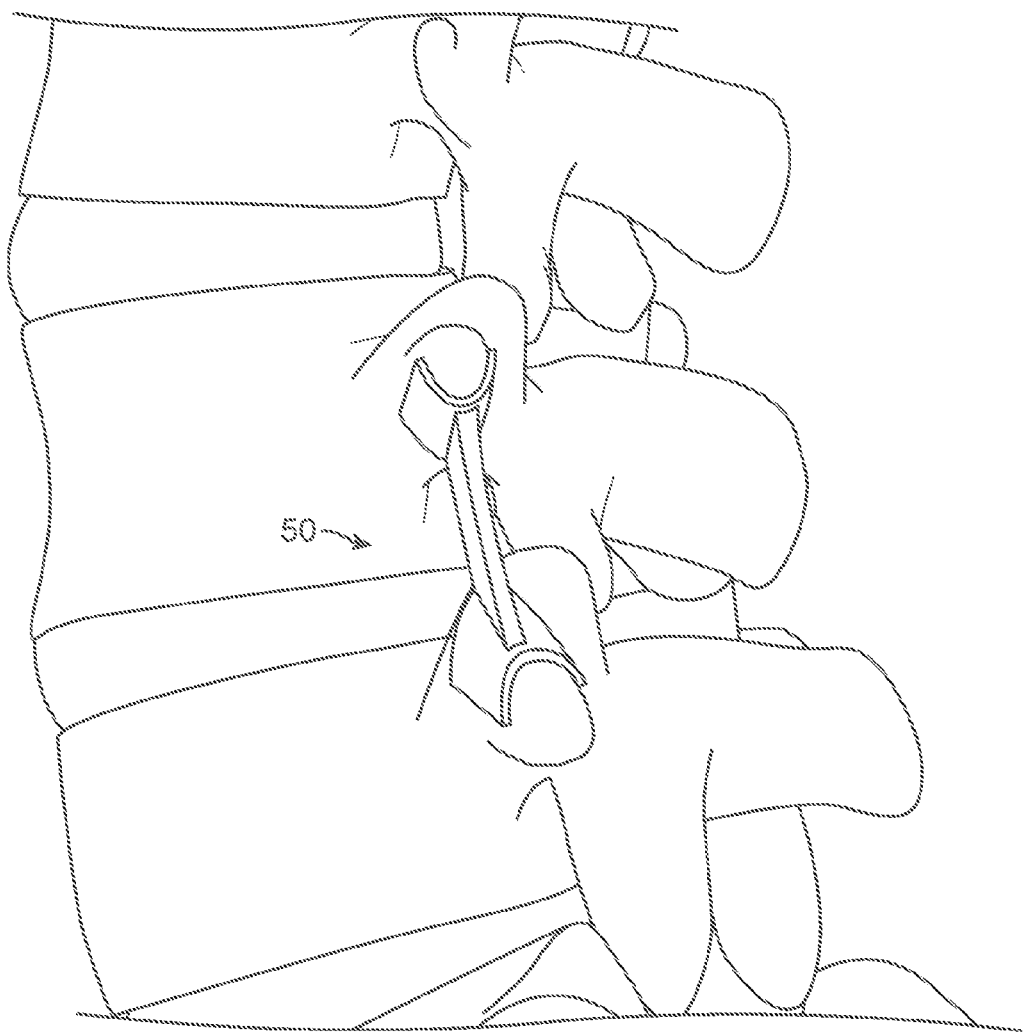
FIG. 9 is a lateral view of the implant of FIG. 8.

FIGS. 6 and 7 depict a still further embodiment of a device as 40, with the device 40 comprising a relatively larger flat plate main body 41 compared to the embodiment depicted in FIGS. 1 and 2. It will be appreciated that in the embodiment where the main body 41 is made of the same material as main body 21, the device 40 will be relatively more rigid than stabilizer device 20 due to the provision of the relatively larger plate. FIGS. 8 and 9 depict a modified device generally as 50 with the main body 51 having a series of holes 52 punched therethrough, thereby modifying the rigidity properties of the device 50 relative to that of device 40. It will be appreciated that devices having fewer or greater holes or holes in different positions could be provided.

Figure 10:
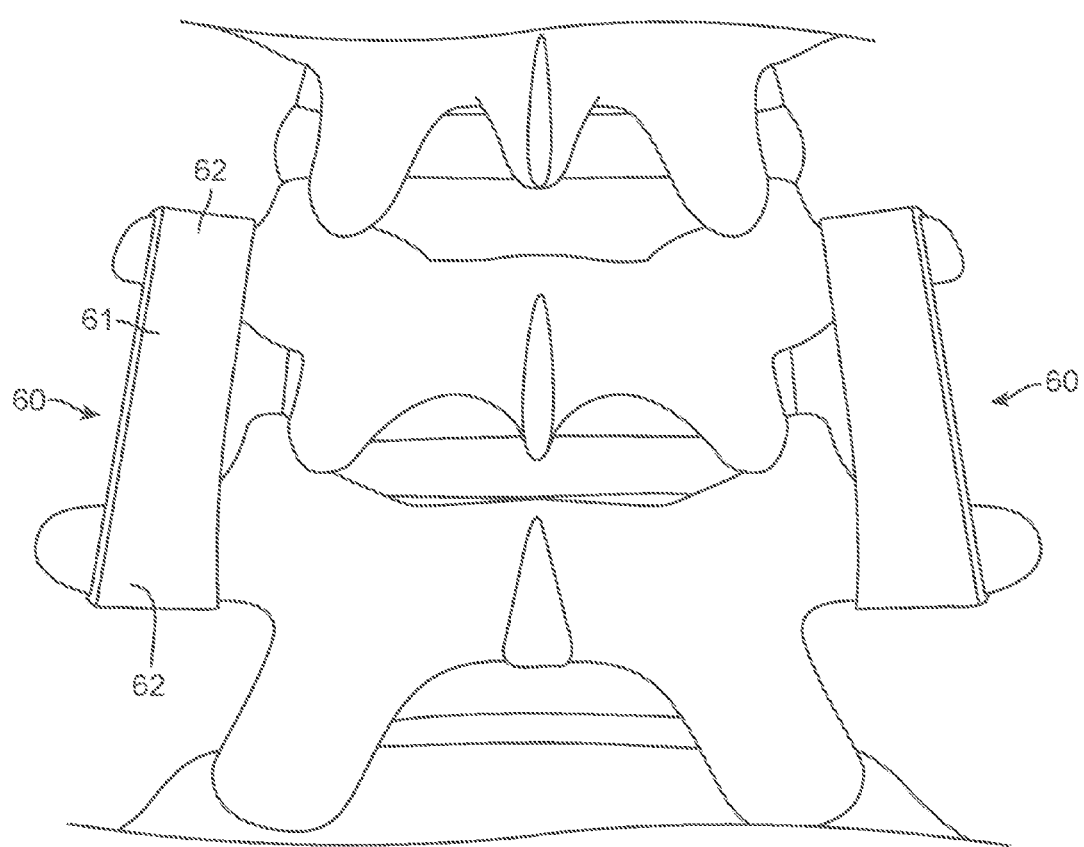
FIG. 10 is a view of an embodiment of a bone stabilizer device.
Figure 11:
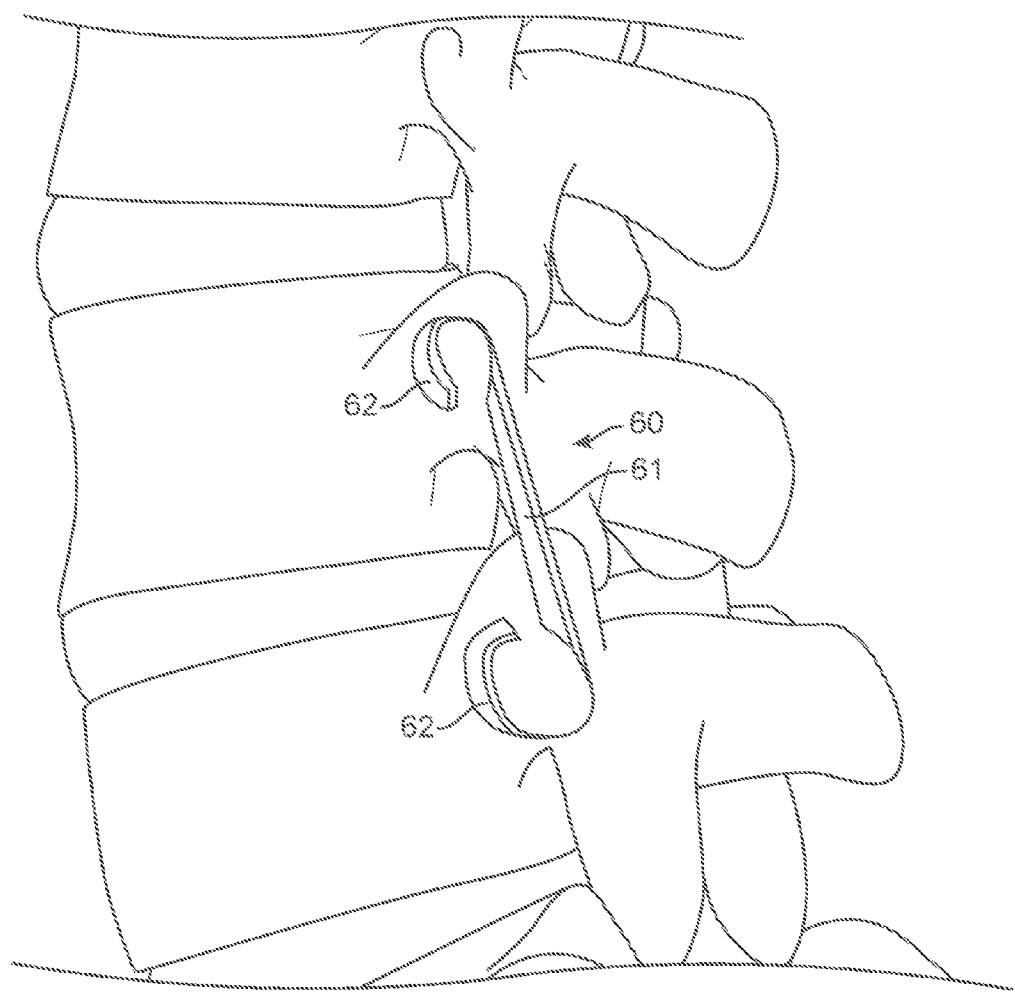
FIG. 11 is a lateral view of the implant of FIG. 10.

Yet another embodiment of a stabilizer device is depicted generally as 60 in FIGS. 10 and 11. In this embodiment, the device 60 comprises a main body 61 and two end engagement portions 62. The device 60 is formed of a deformable material, for example, a metallic mesh material. In this example, the main body 61 and/or end portions 62 can be deformed by the surgeon and so folded or engaged with the bone ends so as to capture the relevant bones. The provision of deformable end portions 62 and/or a deformable main body 61 can also result in a tensile or compressive load between the bone segments as result of the fixation or be performed in a neutral loading aspect. The deformable ability of the end portions 62 and/or the main body can also be used to re-align or reduce any anatomical features that need to be corrected by the surgeon at the time of the surgical procedure.

Figure 12:
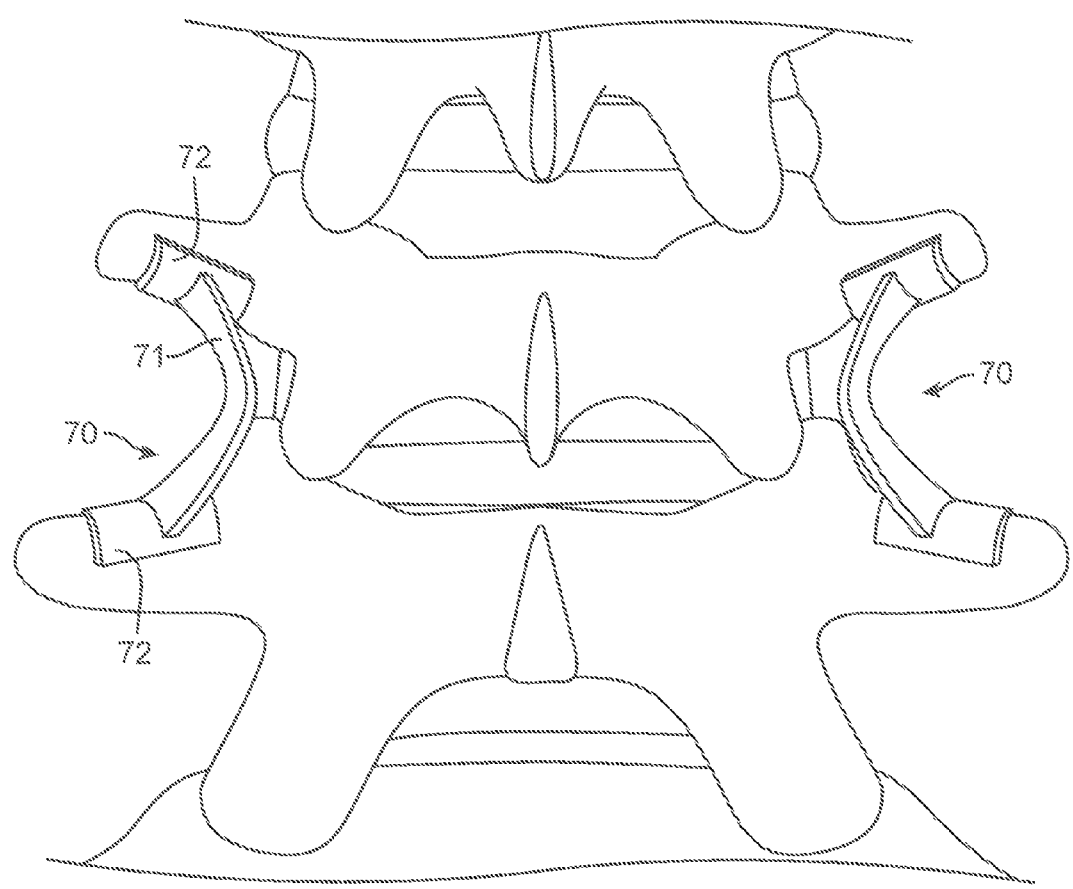
FIG. 12 is a view of an embodiment of a bone stabilizer device.
Figure 13:
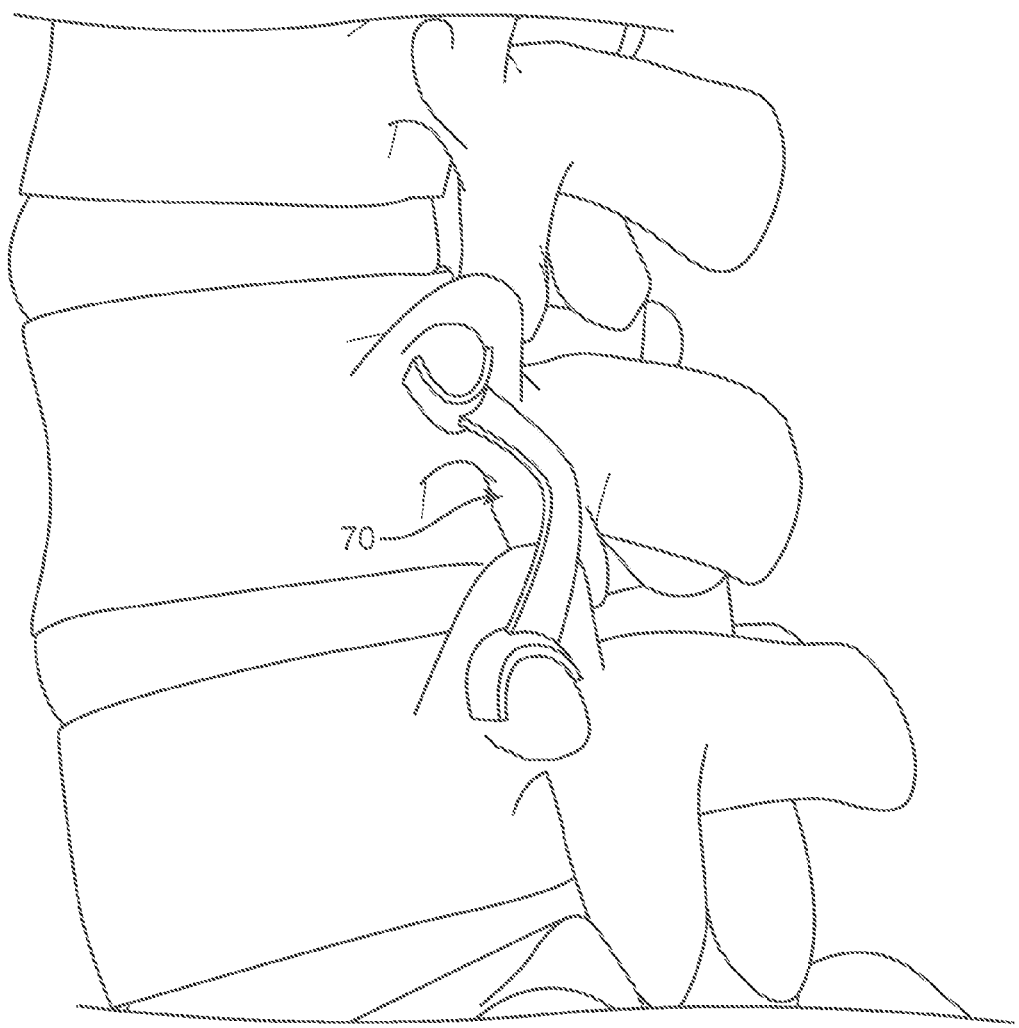
FIG. 13 is a lateral view of the implant of FIG. 12.
Figure 14A:
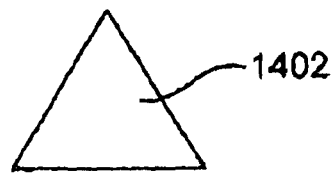
FIG. 14 provides various views of some alternative geometries (cross-sections and shapes) of stabilizer devices as defined herein including those depicted.
Figure 14B:
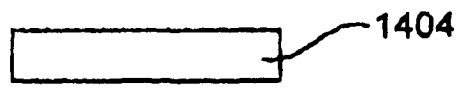
Figure 14C:
Figure 14D:
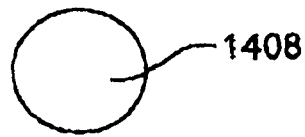
Figure 14E:
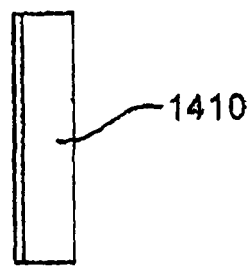
Figure 14F:
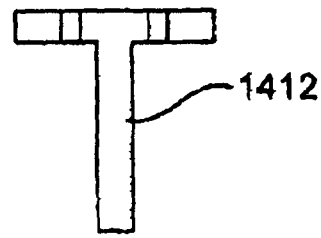
Figure 14G:
Figure 14H:

A still further embodiment is depicted in FIGS. 12 and 13 generally as 70. Here the main body 71 has a leaf spring like configuration and comprises a curved flat plate that extends between two substantially U-shaped portions 72.

While the devices 10-70 are provided with the forms shown, FIG. 14 provides examples of how the respective main bodies of these or other devices could be provided with other cross-sectional shapes or forms. As depicted in FIG. 14, the main body could be provided with triangular, rectangular, crescent-shaped, T-shaped, circular and/or oval cross-sections. The thickness or cross-section shape could vary along the length of the main body between the bone engagement ends.

In some embodiments, the cross section of the bridge may be triangular 1402, rectangular 1404, crescent shaped 1406, circular 1408, multi-layer 1410, t-bar 1412, oval 1414 or irregular 1416 (FIG. 14).

The various configurations, shapes and materials serve to ensure that it is possible for a surgeon to select a stabilizer device that is most suitable for the purpose.

All of the depicted bone stabilizer devices can be formed from a suitable biocompatible material including a metal, a metal alloy or polymeric material or combination thereof. The devices can also comprise an allograft material. The devices can be formed in one piece and alone span the distance between adjacent transverse processes. As depicted, the stabilizer devices can, at least at the time of implantation, comprise a solid one piece member formed from a single material suitable for the purpose of spinal fusion.

The depicted stabilizer devices can be formed from titanium or a titanium alloy. Other suitable metals include stainless steel, cobalt-chromium alloys, and tantalum. Alternatively, metal alloys having varying physical properties such as shape memory capability such as nickel titanium or spring stainless steel alloys may be used. In another embodiment, the devices can be formed from a suitable polymer including non-degradable polymers, such as polyetheretherketone (PEEK) and polyethylene (PE) as well as modified versions of these materials (for example, PEEK+calcium phosphates and PE+vitamin E, or metal coating or surface texturing). Additional non limiting polymers may include polymers, such as polyether-block co-polyamide polymers, copolyester elastomers, thermoset polymers, polyolefins (e.g., polypropylene or polyethylene, including high density polyethylene (HDPEs) and low-density polyethylene (LDPEs) and ultrahigh molecular weight polyethylene (UH-MWPE)), polytetrafluoroethylene, ethylene vinyl acetate, polyamides, polyimides, polyurethanes, polyvinyl chloride (PVC), fluoropolymers (e.g., fluorinated ethylene propylene, perfluoroalkoxy (PEA) polymer, polyvinylidenefluoride, etc.), polyetheretherketones (PEEKs), Polyetherketoneketones (PEKKs), poly(methylmethacrylate) (PMMA), polysulfone (PSU), epoxy resins and silicones. Additionally, starch based polymers may be used.

Additional materials include carbon and polyaramid structures, glass or fiberglass derivatives, ceramic materials, and artificial biocompatible protein derivatives (recombinant derived collagen).

The stabilization device may be made of a metal and/or alloy backbone with a polymer shell, or a sandwich style composition of any number of layers of any of the materials listed herein. Various layers may be bonded to each other to provide for single layer composition of metal(s) and/or alloys and/or polymers. In another embodiment, a polymer backbone may be used with a metal and/or metal alloy shell.

In various embodiments, various materials may be used to facilitate, stimulate or activate bone growth. A non-limiting list of materials may include hydroxyapatite (HA), synthetic bioabsorbable polymers such as poly($\alpha$-hydroxy esters), poly(L-lactic acid) (PLLA), poly(glycolic acid) (PGA) or their copolymers, poly(DL-lactic-co-glycolic acid) (PLGA), poly(ε-caprolactone) (PLC).

In some embodiments, the device is substantially free of osteogenic biochemical and/or biological agents. These agents include, but are not limited to, autografts, such as autogenous bone marrow, platelet-rich plasma, cancellous autograft, cortical autograft; allografts, such as cancellous allograft, cortical allograft, massive osteochondral allograft, demineralized bone matrix; osteogenic growth factors and cytokines, such as bone morphogenic proteins (BMPs) of various origins and in various carriers; and any combinations thereof. In yet other embodiments, the present device may optionally be used in conjunction with these agents, either incorporated in the device, provided in a kit, or used separately, as appropriate.

The bone engagement or integration portions (e.g., the substantially U-shaped members in FIG. 1) can comprise a three-dimensional space to allow bone integration into and/or onto the portions. The three-dimensional space can be provided by a three-dimensional substrate, for example beads, and/or by the provision of holes through the bone integration portions. Other methods for achieving bone integration can include the provision of an appropriate surface topography, for example a roughened or textured area and/or by the provision of osteoconductive coatings, such as calcium phosphates.

As depicted by the examples of FIGS. 10 and 11, the main body 61 of the device 60 can also comprise a three dimensional space to allow bone integration into and/or onto the main body 61. The three-dimensional space can be provided by a three-dimensional substrate, for example beads, and/or by the provision of holes through the main body. Other methods for achieving bone integration can include the provision of an appropriate surface topography, for example a roughened or textured area and/or by the provision of osteoconductive coatings, such as calcium phosphates onto the main body 61. In this regard, the device itself can provide a metal and/or polymeric scaffold for tissue integration to be achieved through the device.

The integration of bone ingrowth or ongrowth to the device at the bone implant interface provides a biological stabilization while initial fixation can be achieved through the use of various fixation techniques including suture, screws, staples or the geometry of the device alone through dimensions or by deforming the geometry at the time of implant to provide a close approximation to the bone bed.

The bone stabilizer devices 10-70 and the method of stabilizing as defined herein have a number of advantages and features. No screws, staples, clips, semi-permanent sutures, unnatural bioadhesives or bolts are required to achieve fixation of the stabilizer to the host bone in one form on the device(s) but they can be used as well. In addition, synthetic or autogeneous materials in the form of particulates or granules and the like are not required to induce fixation of the stabilizer and subsequent fusion.

The ability to select a suitable stabilizer having the features as defined also allows calculations to be made that are far more accurate and practical than is the case when fusion is based on use of stabilizers formed of particulate or granular materials or where screws or other mechanical fasteners are used. Use of the stabilizer as defined can facilitate meaningful calculations relating to post-operative flexural extension, lateral bending and/or axial rotation. It also serves to lessen or avoid the risk of adjacent segment disease and, in the case of spinal fusion, degeneration of the discs as well as changes to the bone of the vertebral body.

The constructions and properties of the bone integration portions provide relatively quick and stable fixation of the stabilizer to the host bone(s) and avoids the relatively long time required to achieve biological fixation with traditional autograft/allograft/synthetic bone graft materials that are particulate in nature and require the body to integrate through them to achieve ultimate stability.

Figure 15:
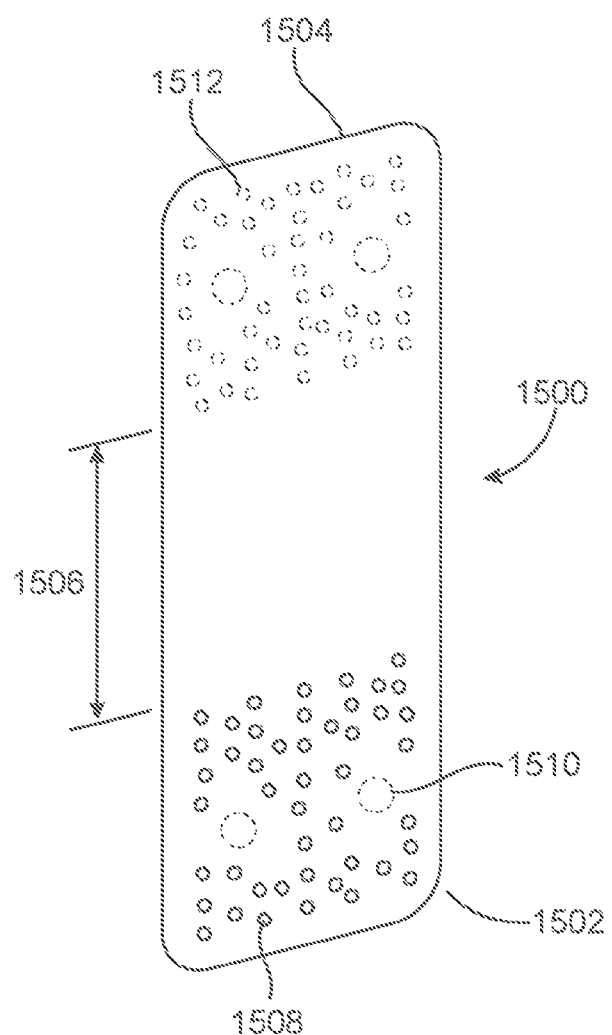
FIG. 15 is a view of an embodiment of a bone stabilizer device.
Figure 20:
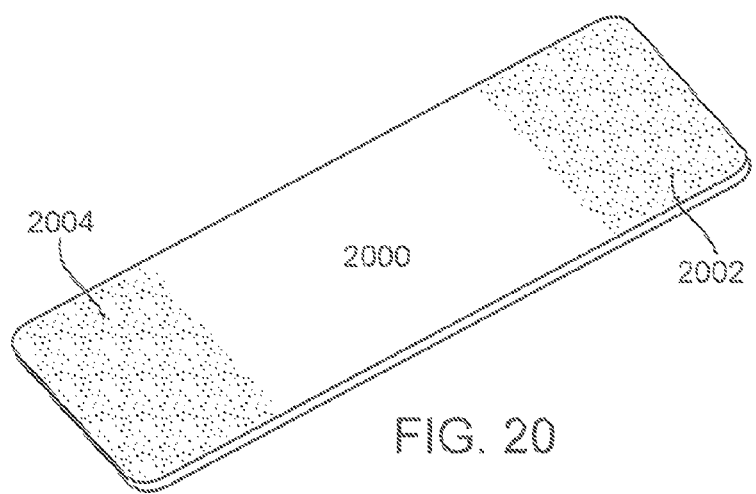

In an embodiment, there is a generally rectangular or parallelogram shaped bone stabilizer 1500 with a generally flat body. The body has two ends 1502, 1504. One end 1502 has a bone engagement feature 1508. The second end 1504 optionally has a bone engagement feature 1512. The two ends 1502, 1504 are separated by a middle section or bridge 1506. In some embodiments, the bone engagement feature 1508 may be one or more perforations in the body (FIG. 15). Additional optional holes 1510 may be provided to allow fasters such as screws, nails or pegs, to pass through the body 1500. The perforations may be of varying sizes with regular or random pattern. The perforations may have a minimum width of material between the perforations (holes) or may have random distances between each perforation. In some embodiments, the bone engagement feature may be porous like zone of material created as part of the body, or as a layer added to the body 1600. In some embodiments, the porous nature may extend from a few microns down from one surface 1602 (FIG. 16) or the porous nature of the material may extend throughout the body structure. The porous layer may be a separate layer of the same or a different material bonded or otherwise fixed to the body 2000. In some embodiments, the bone engagement feature may be a roughened or etched surface 2002, 2004 that provides a non-smooth surface for contacting the bone (FIG. 20). The roughened surface similarly assists in bone ongrowth to the bone stabilizer device.

Figure 17:
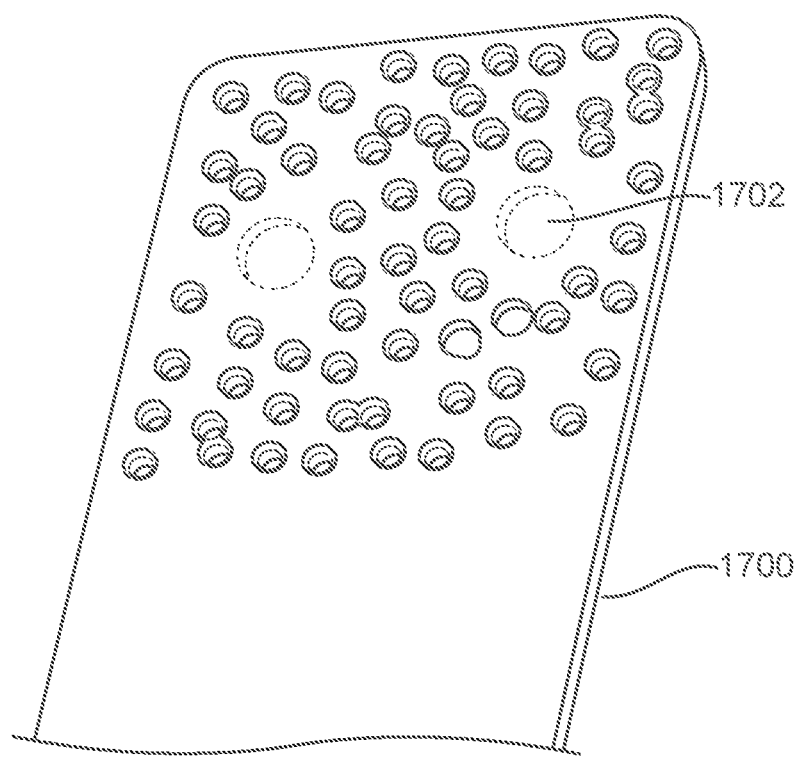
FIGS. 17-21, 22A-C are views of several embodiments of a bone stabilizer device.
Figure 18:
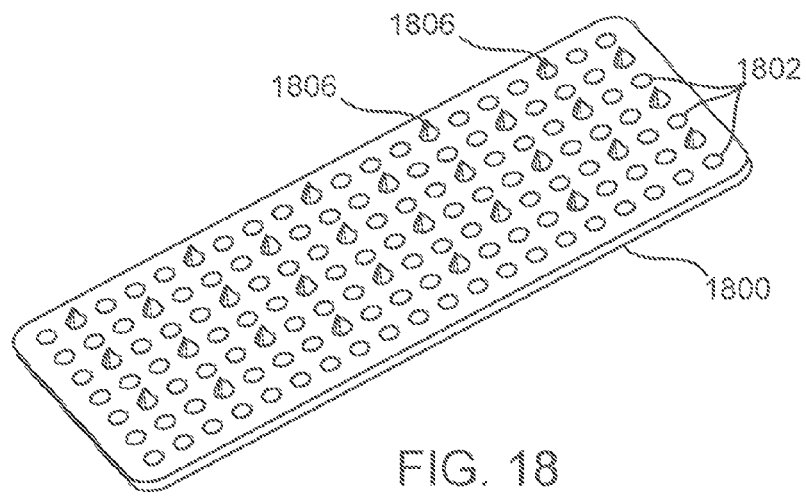
Figure 19:
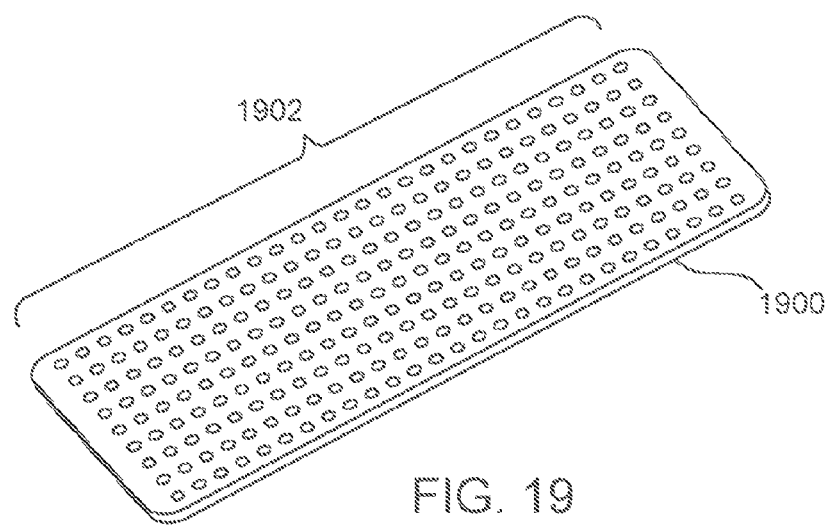
Figure 21:
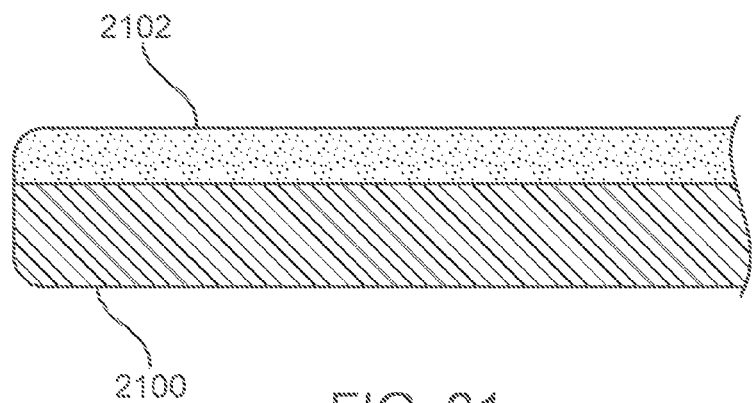
Figure 22:
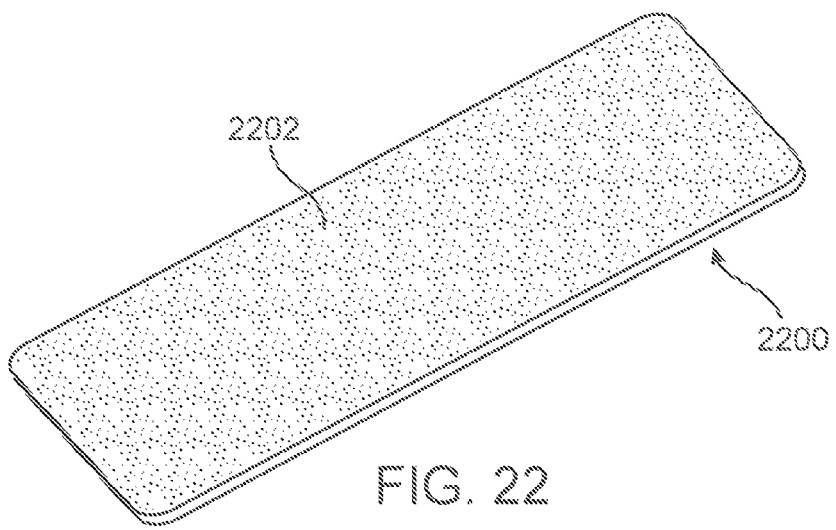
Figure 23:
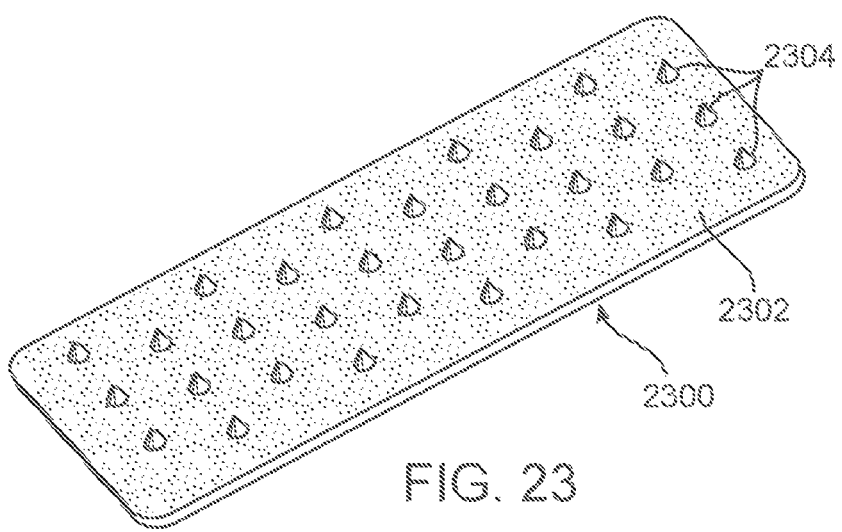

In some embodiments, the first and second end may have larger holes 1710 for through which additional fasteners may be placed (such as screws, nails or pegs) (FIG. 17). An enlarged view of one end of the bone stabilization ends (FIG. 17) shows the device 1700 and optional apertures 1702 for additional fasteners. In some embodiments, the bone engagement feature may continue along the entire length of the body (first end, second end and bridge) (FIGS. 19 and 22). In some embodiments, the bone engagement feature may also have a bone integration feature (FIG. 18) in the form of spikes, nails, pins or other fasteners that may pierce the outer layer of bone and penetrate deep enough to stimulate a wound healing response. In an embodiment, the device 1800 has both a bone engagement feature 1802 and a bone integration feature 1806 (FIG. 18). In an embodiment, the device 1900 has a bone integration feature 1902 that extends the entire length of the device (FIG. 19). In an embodiment, the bone stabilization device may have a body 2100 with a bone engagement feature 2102 layered on it (FIG. 21). In an embodiment, the bone stabilization device 2200 may have a continuous bone engagement feature 2202 (FIG. 22). In some embodiments, the roughened surface 2302 may have one or more bone integration features 2304 (FIG. 23), or may have the roughened surface along the entire length of the bone stabilizer device (FIG. 22). In an embodiment, the bone stabilization device 2300 may have a continuous bone engagement surface 2302 in the form of a roughened or etched surface with one or more bone integration features 2304 (FIG. 23). The roughened surface may be part of the bone stabilization device 2100 or may be a layer 2102 of material added on to the device (FIG. 21). The bone engagement surface may be a combination of a porous section of the body, combined with a roughened or etched surface.

Figure 24:
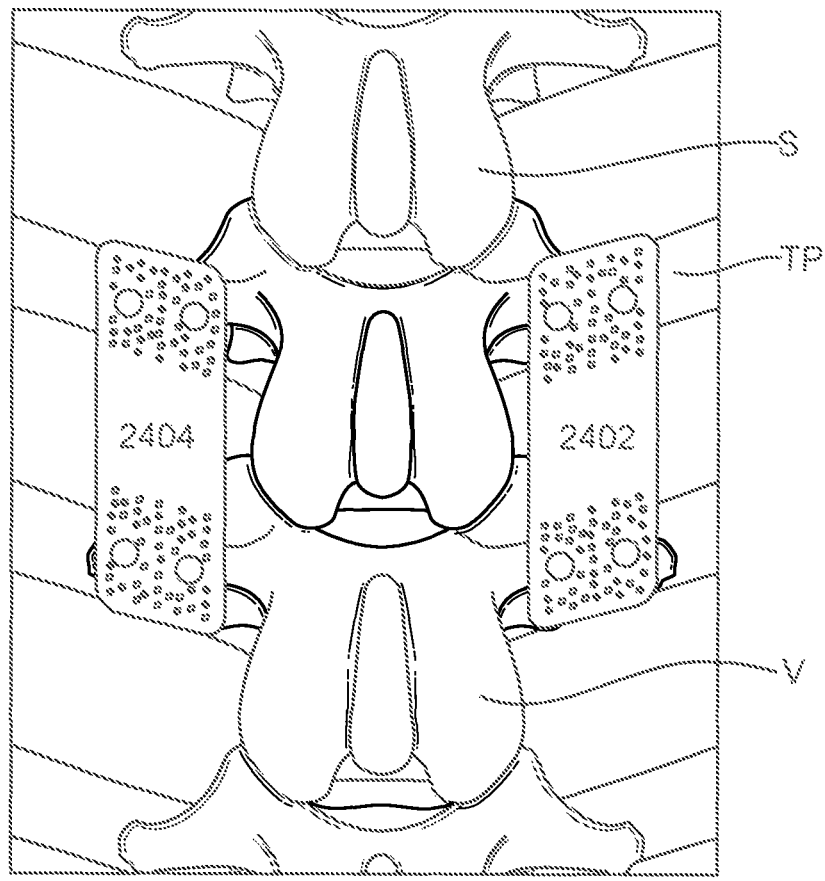
Figure 25:
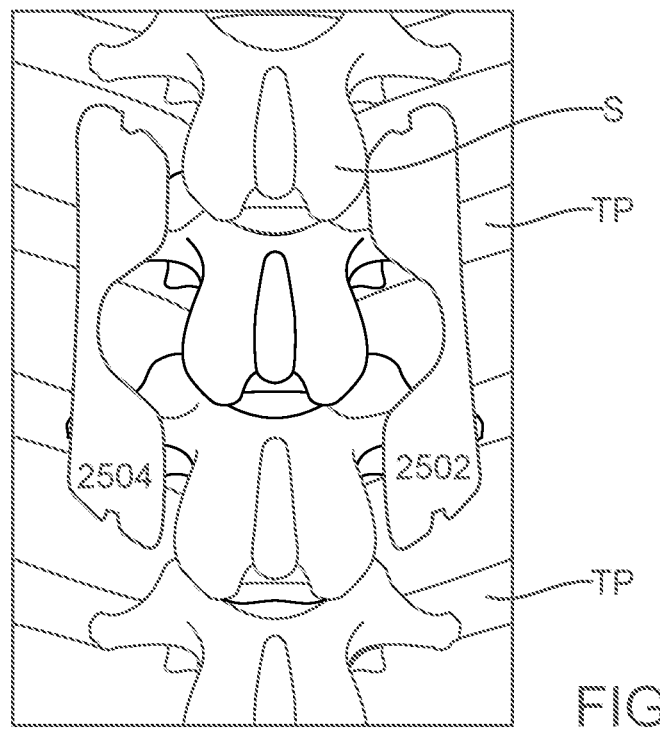
FIGS. 25 and 26 show embodiments of a bone stabilizer device.
Figure 26:
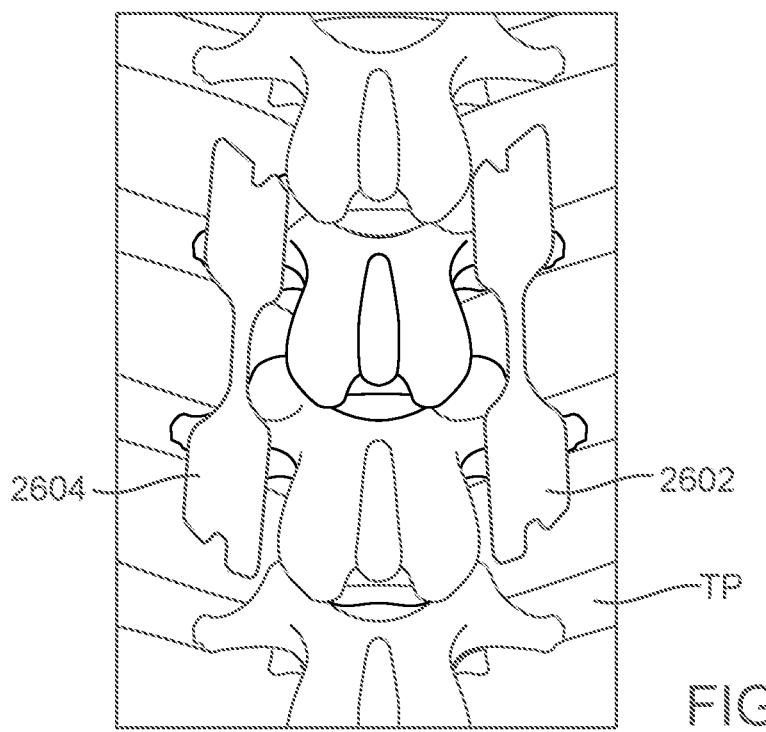

In one aspect, a pair of bone stabilization devices 2402, 2404 may be laid across two adjacent transverse processes on the same side of the spine (FIG. 24). The bone stabilization device may be laid across the transverse processes with or without additional fixation mechanisms (such as sutures, screws or clamps). In some embodiments a pair of bone stabilization devices may be used, one on each side of the spine. In other embodiments, the bone stabilization device may be adapted for use on the spine facets or to be used on any two adjacent bones in the body. In some embodiments, the bone stabilization device may have a bridge portion that is of a different size than the first and second end. The middle or bridge portion may be curved to form a thinner region, may have a reinforcement bar across it (like a T-bar) or it may have additional features desired by the surgical team or manufacturer to provide a better bonding experience. In some embodiments, the bridge is shifted to one side (FIG. 25) or tapered to have a single support structure down the middle (FIG. 26). The anatomy of the patient is shown with the spine S and transverse processes TP (FIG. 25).

Figure 27A:
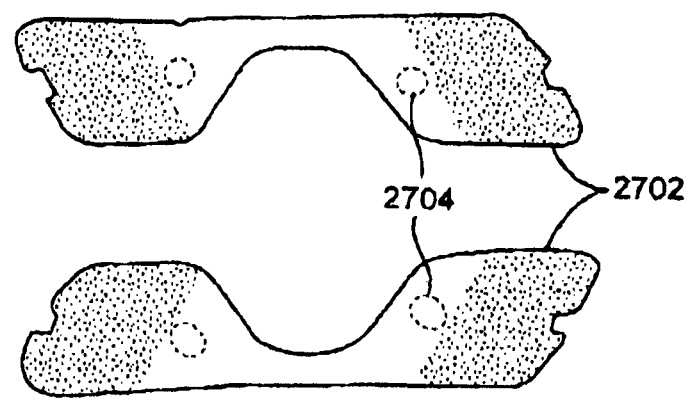
Figure 27B:
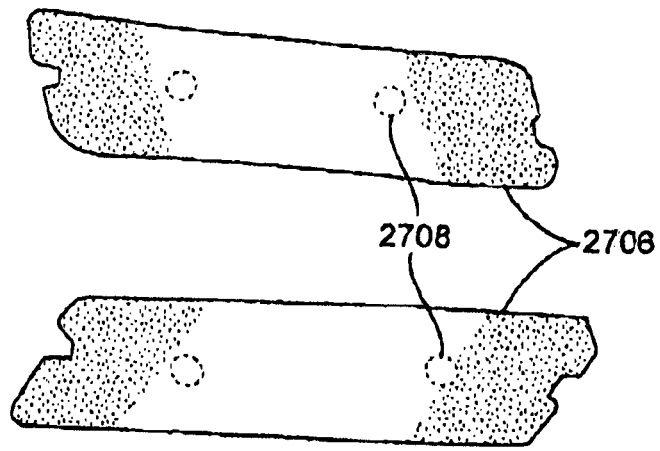
Figure 27C:
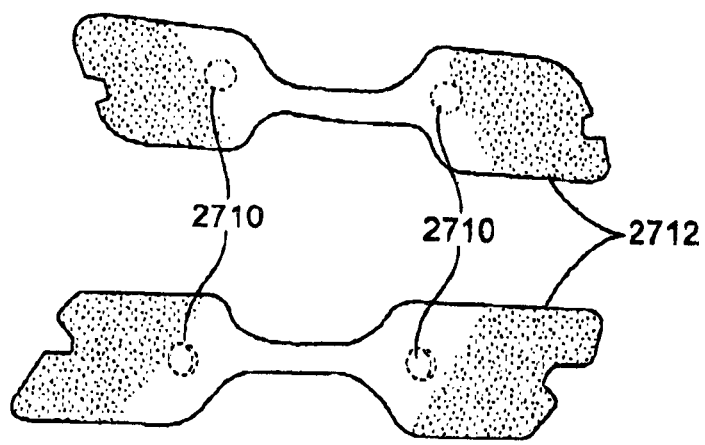
Figure 28A:
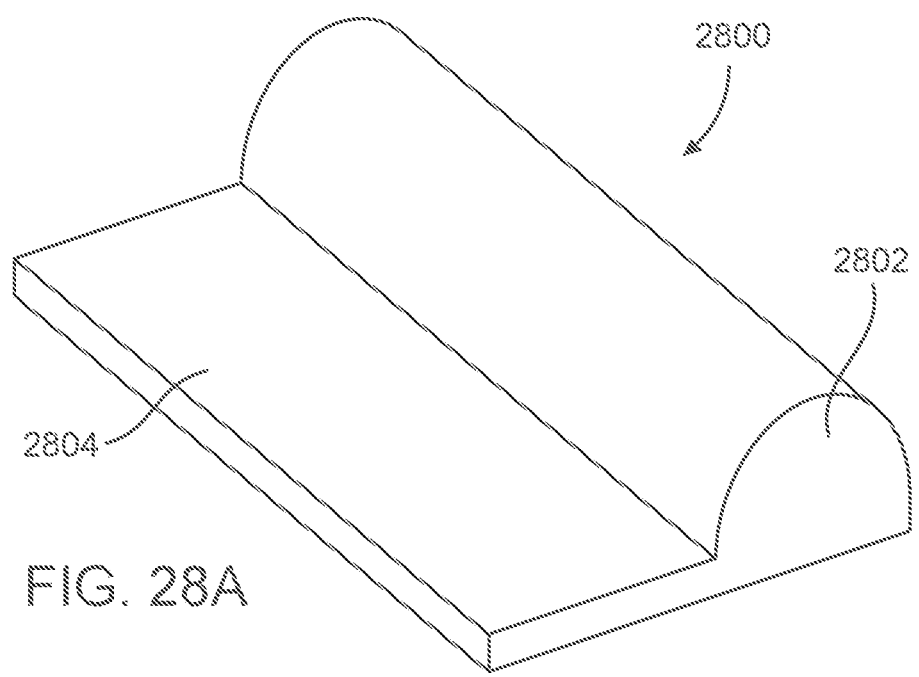
FIGS. 28A, 28B are top and bottom perspective views, respectively, of an embodiment of a bone stabilizer device.
Figure 28B:
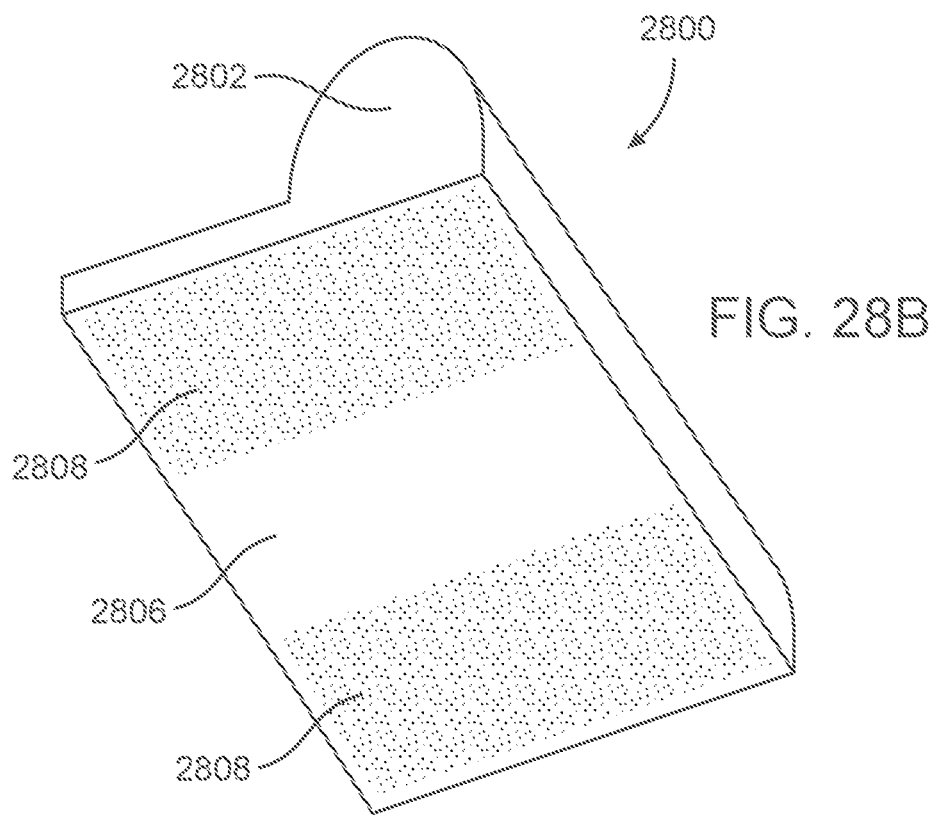
Figure 29A:
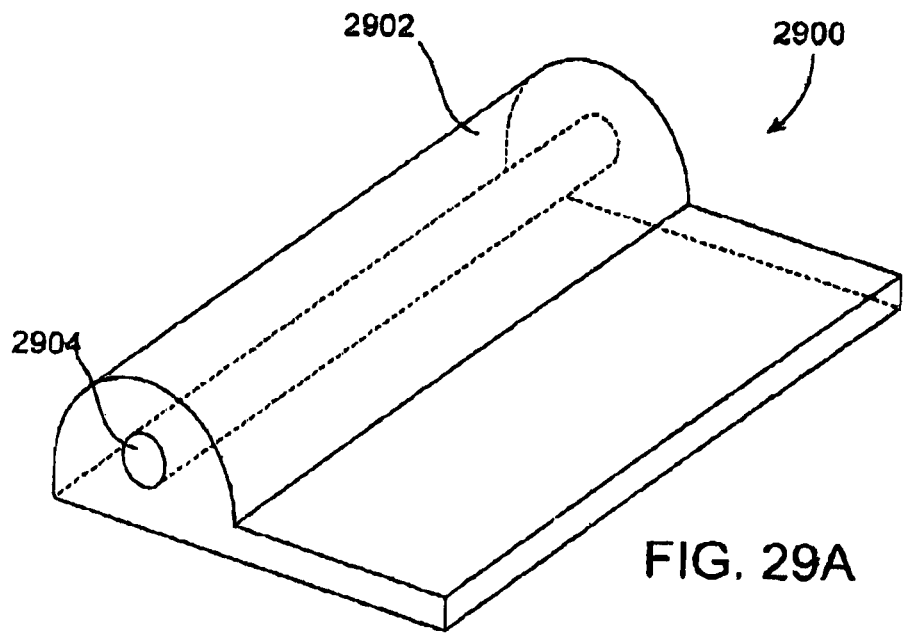
FIGS. 29A, 29B are top and bottom perspective views, respectively, of an embodiment of a bone stabilizer device.
Figure 29B:
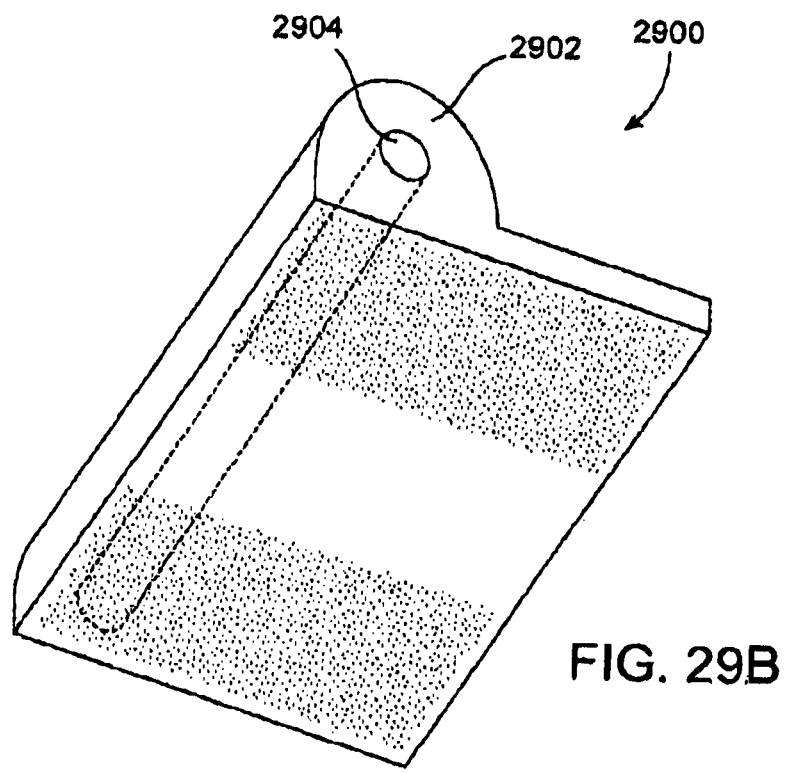

Alternative embodiments where the bridge or middle portion has a lower relative aspect ratio than the first and second ends are provided in FIG. 27. The designs in FIG. 27 are illustrative only and should not be considered exhaustive. Many possible designs are conceivable and all of them are intended to be covered herein. In some embodiments, there may be two bridge elements or more. In some embodiments, the bridge may be displaced to one side 2702 with optional apertures for fasteners 2704. Alternatively, the bridge may be generally about the same width as the first and second end 2706, again with optional apertures 2708. In still other embodiments, the bridge may be narrow and centered 2712 with optional apertures 2710.

In an embodiment, the bone engagement feature may serve to facilitate the integration of the stabilization device to the natural bone. Decortication of bone prior to placement of the bone stabilization device produces a bone healing response (osteogenesis). As the bone healing response occurs, the new bone growth may intertwine, surround or overgrow the bone engagement feature of the bone stabilization device. Thus, the bone engagement feature provides an improved footing through which bone growth can integrate the stabilization device. Full integration of the bone stabilization device to the bone may occur in as little as six weeks.

In an embodiment, the stabilization device may be made from a material that degrades slowly over time, such that the growth of bone over the bone stabilization device is equal to or exceeds the rate of decay of the bone stabilization device. In some embodiments, the bone stabilization device may have some elements or components that are persistent (do not decay) and some elements that do decay. By decay, it is meant that the elements and/or materials of the stabilization device are bioabsorbable or biodegradeable.

The dimensions of the bone stabilizer device will depend on their required use and materials. For example, the length and width of the body may be different if the stabilization devices are used to fuse transverse processes of cervical vertebrae versus thoracic vertebrae or lumbar vertebrae. Because the distance between adjacent transverse processes of cervical vertebrae is different to the distance between transverse processes of thoracic vertebrae, and to transverse processes of lumbar vertebrae. Furthermore, height, or thickness of bone stabilizers may also be different, depending on the amount of rigidity desired. For example, loads experienced in the cervical vertebrae are lower than loads experienced in lumbar vertebrae. Examples of dimensions of the bone stabilizers of titanium alloy to span adjacent cervical transverse processes might include a length from 30-90 mm, a maximum width of 25 mm, and a thickness of 1-10 mm. To span thoracic transverse processes, a length may be 40-120 mm, a maximum width 50 mm and a thickness of 1-20 mm. To span lumbar transverse processes, a length may be 60-180 mm, a maximum width 40 mm and a thickness 1-35 mm. For titanium alloy, this would provide a rigidity of about $9 \times 10^{-3}$ $Nm^2$ or higher. Of course, this could be lower, such as $5.5 \times 10^{-3}$ $Nm^2$, should the thickness be reduced further to 0.5 mm.

Further embodiments of the bone fusion device are illustrated in FIGS. 28A-35B. In these embodiments, the bone fusion device has a thickened portion to increase rigidity of the device. This may be useful where the device is formed from polymer, however is not limited to embodiments formed from polymers. In the device 2800 illustrated in FIGS. 28A, 28B, the thickened portion 2802 is located toward a side of the device 2800. The thickened portion 2802 is also located on a face 2804 of the device 2800 that is opposite a face 2806 on which bone engagement features in the form of a textured surface 2808 is located. An alternative embodiment of a bone fusion device 2900 is illustrated in FIGS. 29A, 29B, which has a similar geometry to the device illustrated in FIGS. 28A, 28B, having a thickened portion 2902 on one side of the device 2900. However, in this embodiment, the thickened portion 2902 has a reinforcement element in the form of a rod 154, which runs the length of the device 2900 in the thickened portion 2902. As will be understood, in alternative embodiments, the reinforcement element may not run the length of the device, but only partially.

FIGS. 30A-35B illustrated alternative embodiments, where the thickened portion is located centrally of the device, such as illustrated in FIGS. 30A-33B, or where the thickened portion is narrower than either of the first or second ends with respect to an axis of the device between the first and second ends. In an embodiment, there is a device 3200 having first and second ends 3202, 3204, and a thickened bridge portion 3206 between the two ends 3202, 3204 (FIGS. 32A, 32B). The thickened bridge portion 3206 is narrower than the two ends 3202, 3204 with respect to the device axis. The device 3300 (FIGS. 33A, 33B) is similar, however also includes a reinforcement element in the form of a rod 3302. The device 3400 (FIGS. 34A, 34B) also has a thickened bridge portion 3402 narrower than the two ends 3404, 3406, however the thickened bridge portion 3402 of the device 3400 of this embodiment is located to the side of the device 3400.

Figure 30A:
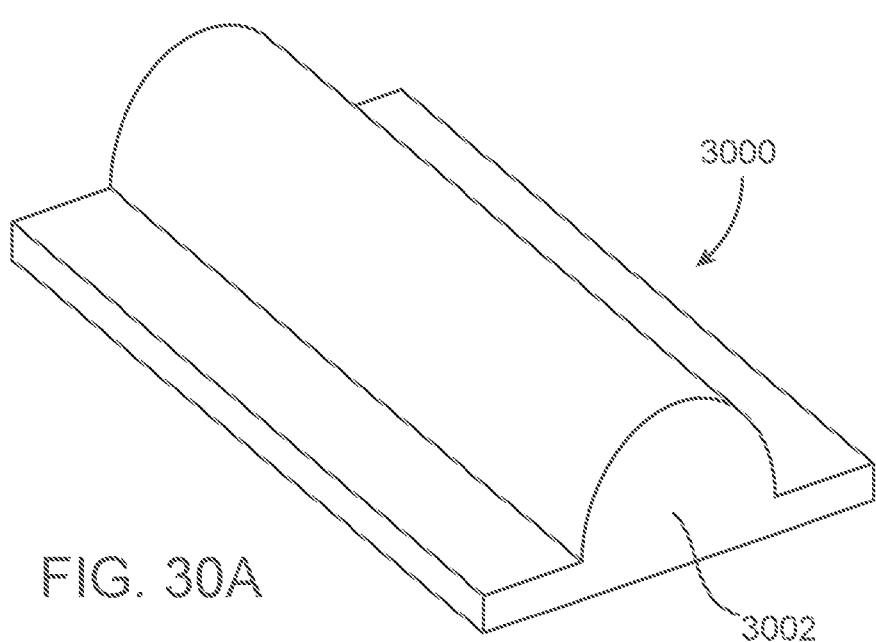
FIGS. 30A, 30B are top and bottom perspective views, respectively, of an embodiment of a bone stabilizer device.
Figure 30B:
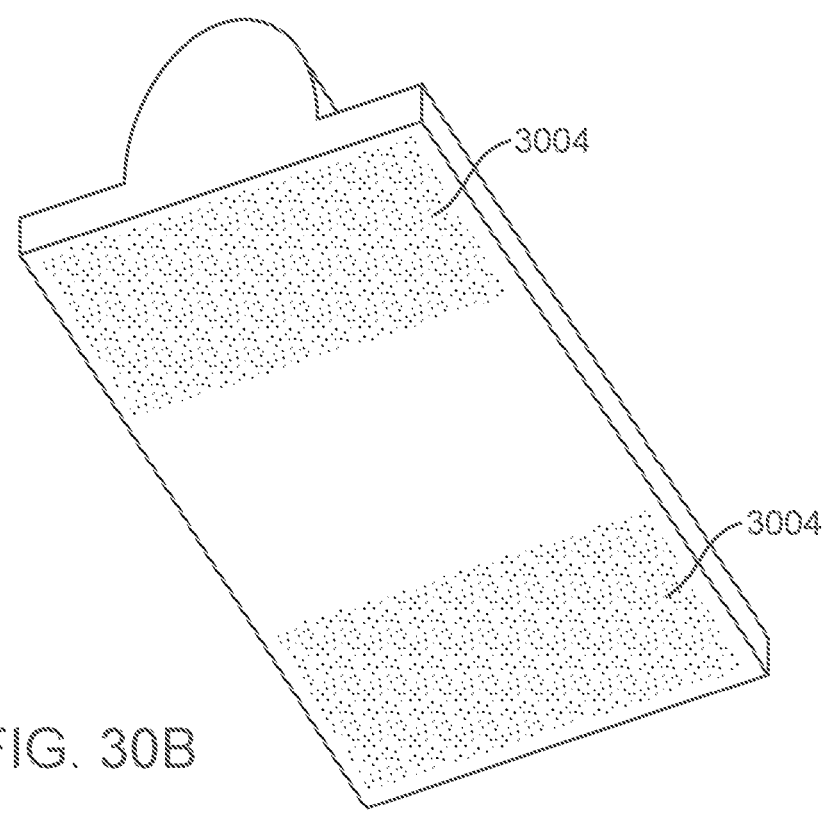
Figure 31A:
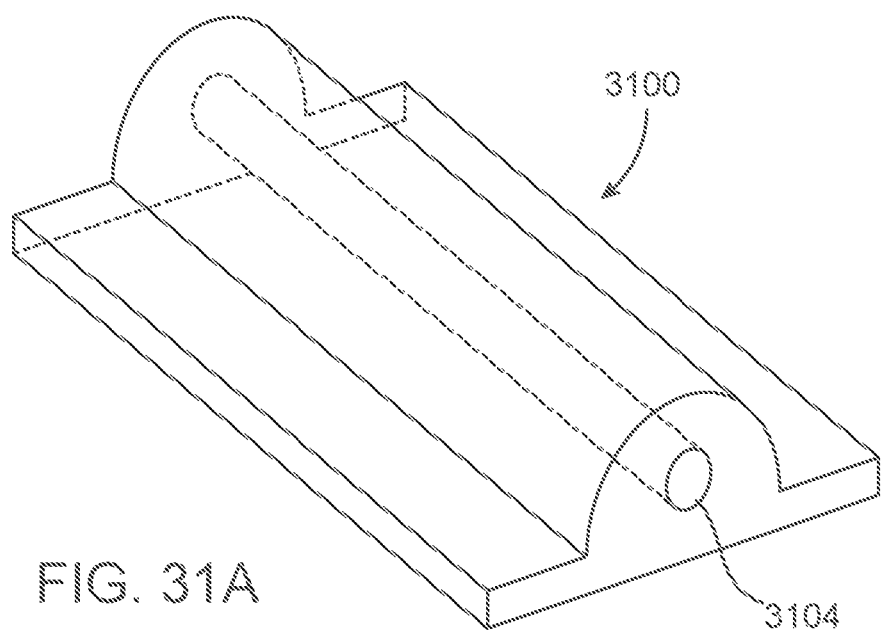
FIGS. 31A, 31B are top and bottom perspective views, respectively, of an embodiment of a bone stabilizer device.
Figure 31B:
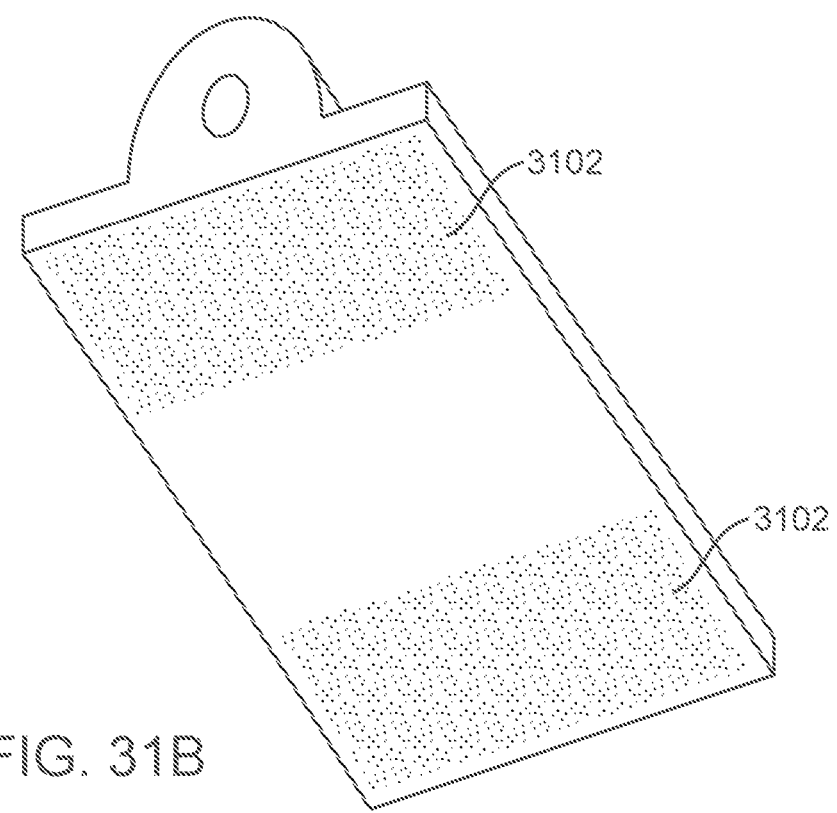
Figure 32A:
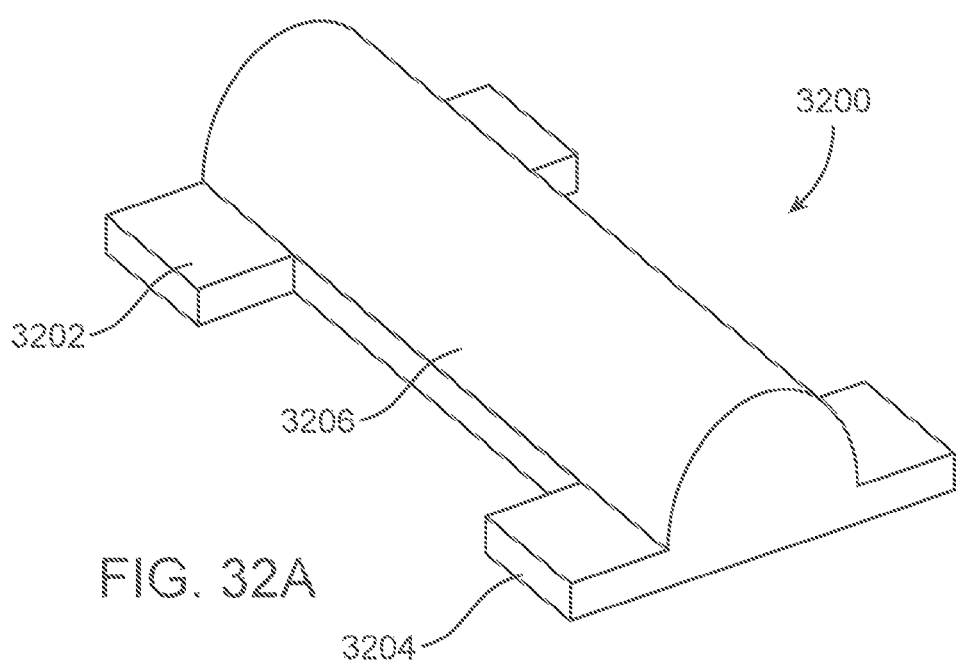
FIGS. 32A, 32B are top and bottom perspective views, respectively, of an embodiment of a bone stabilizer device.
Figure 32B:
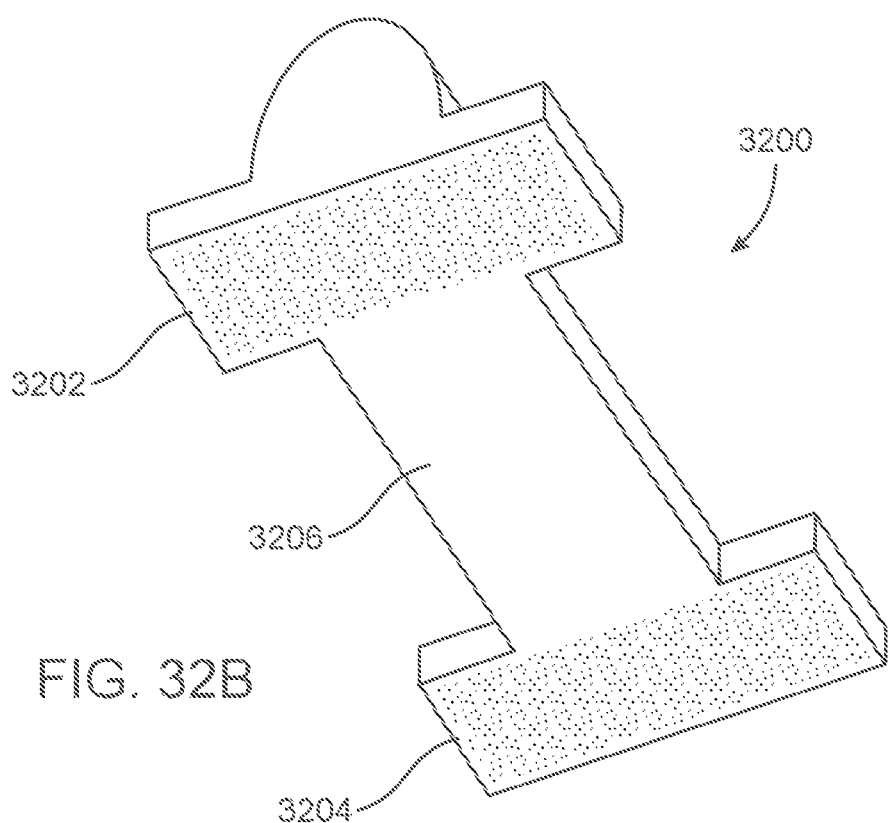
Figure 33A:
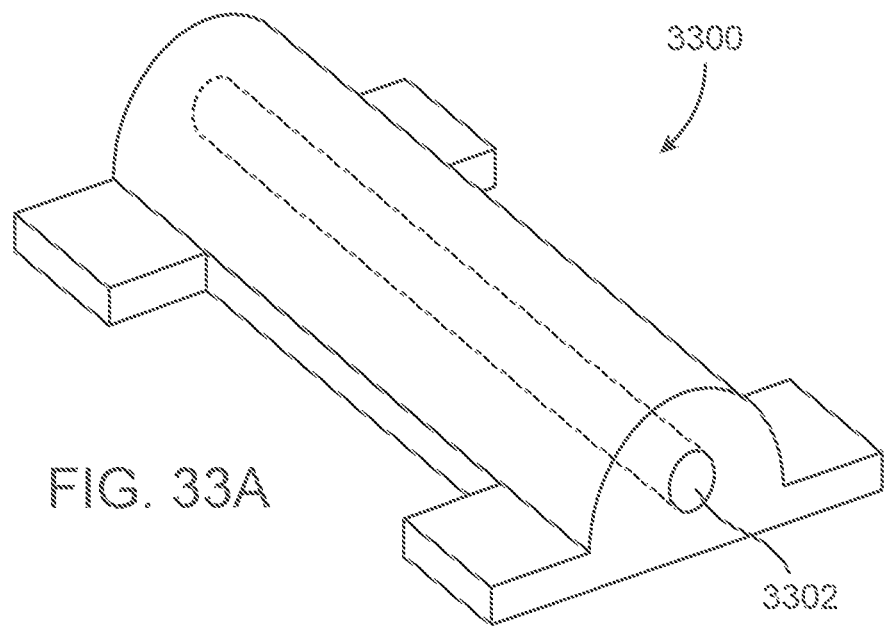
FIGS. 33A, 33B are top and bottom perspective views, respectively, of an embodiment of a bone stabilizer device.
Figure 33B:
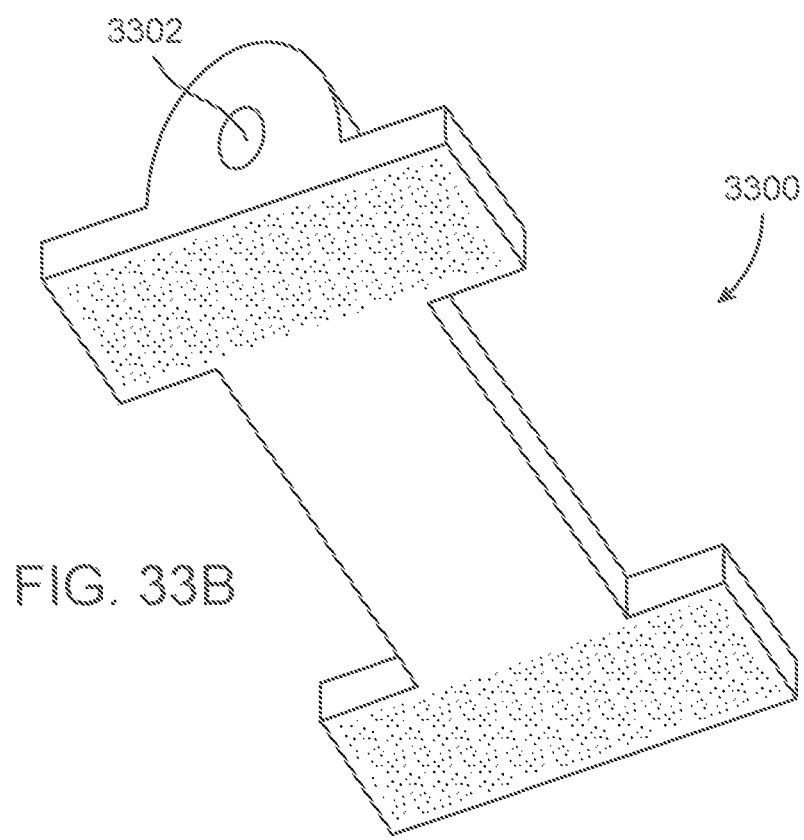
Figure 34A:
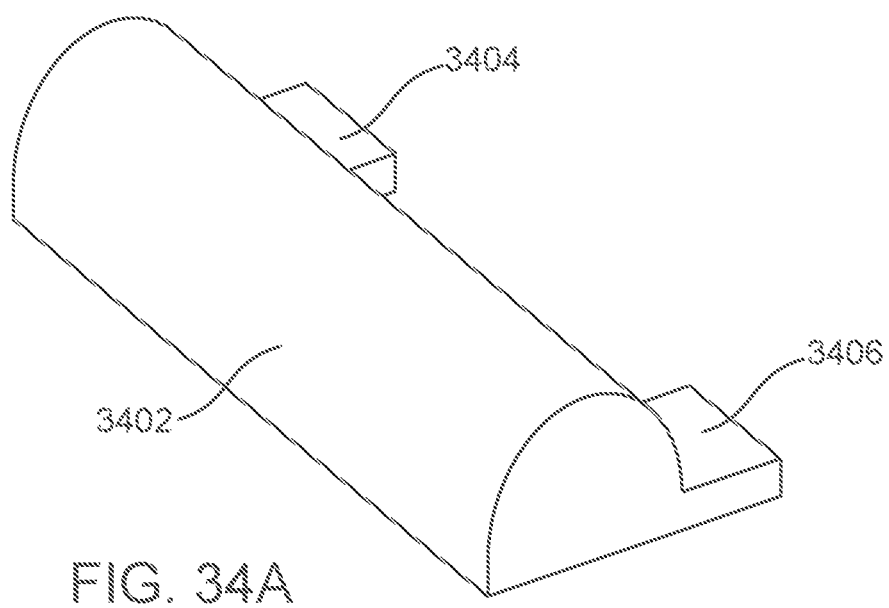
FIGS. 34A, 34B are top and bottom perspective views, respectively, of an embodiment of a bone stabilizer device.
Figure 34B:
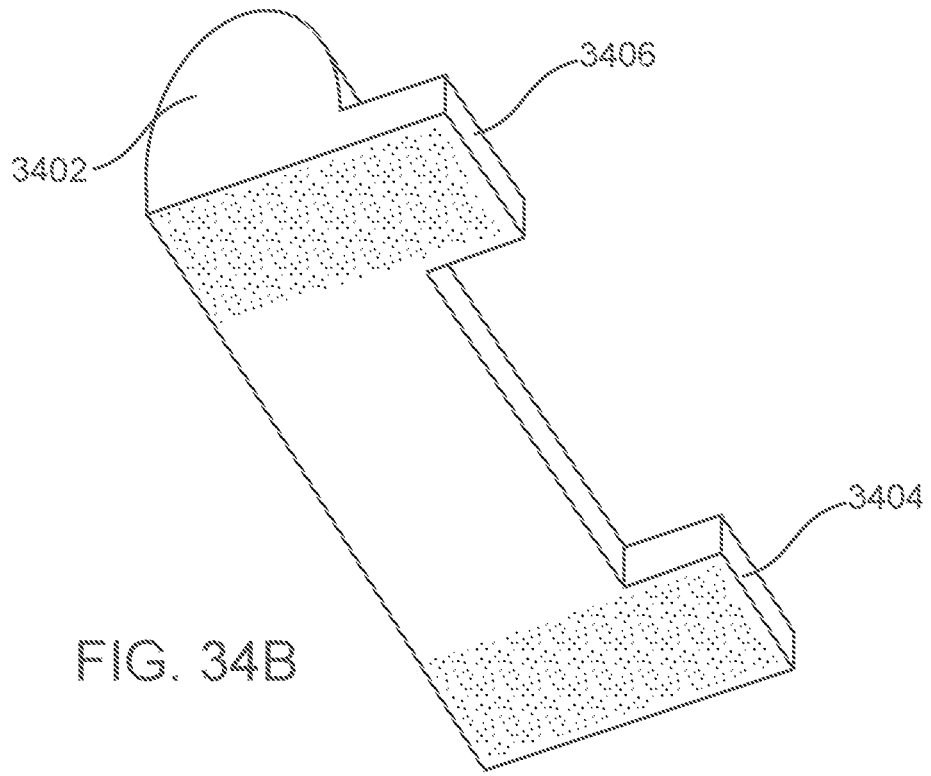

In an embodiment, the device 3000 may have a center positioned reinforcement feature 3002 and one or more bone engagement feature(s) 3004 (FIG. 30A-30B). In an embodiment, the device 3100 may have a central bore tube 3104 for placement of a reinforcement bar, or remain hollow to provide structural flexibility or an avenue for bone ingrowth (FIG. 31A). One or more bone engagement features 3102 may also be provided (FIG. 31B).

The designs shown in the drawings are illustrative only and should not be considered exhaustive. Many possible designs are conceivable and all of them are intended to be covered herein. In some embodiments, there may be two bridge elements or more.

In one aspect, the bone stabilization device may be laid across two adjacent transverse processes on the same side of the spine (FIG. 24). The bone stabilization device may be laid across the transverse processes with or without additional fixation mechanisms (such as sutures, screws or clamps). In some embodiments, a pair of bone stabilization devices may be used, one on each side of the spine. In other embodiments, the bone stabilization device may be adapted for any two adjacent bones in the body.

In an embodiment, the bone engagement feature may serve to facilitate the integration of the stabilization device to the natural bone. Decortication of bone prior to placement of the bone stabilization device produces a bone healing response (osteogenesis). As the bone healing response occurs, the new bone growth may intertwine, surround or overgrow the bone engagement feature of the bone stabilization device. Thus, the bone engagement feature provides an improved footing through which bone growth can integrate the stabilization device. Full integration of the bone stabilization device to the bone may occur in as little as six weeks.

In an embodiment, the stabilization device may be made from a material that degrades slowly over time, such that the growth of bone over the bone stabilization device is equal to or exceeds the rate of decay of the bone stabilization device. In some embodiments, the bone stabilization device may have some elements or components that are persistent (do not decay) and some elements that do decay. By decay, it is meant that the elements and/or materials of the stabilization device are bioabsorbable or biodegradeable.

Figure 35A:
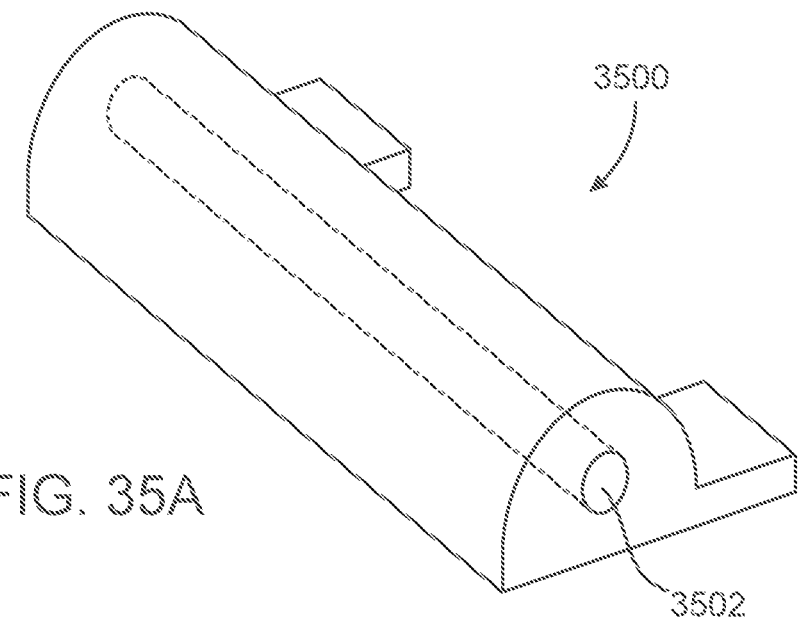
FIGS. 35A, 35B are top and bottom perspective views, respectively, of an embodiment of a bone stabilizer device.
Figure 35B:
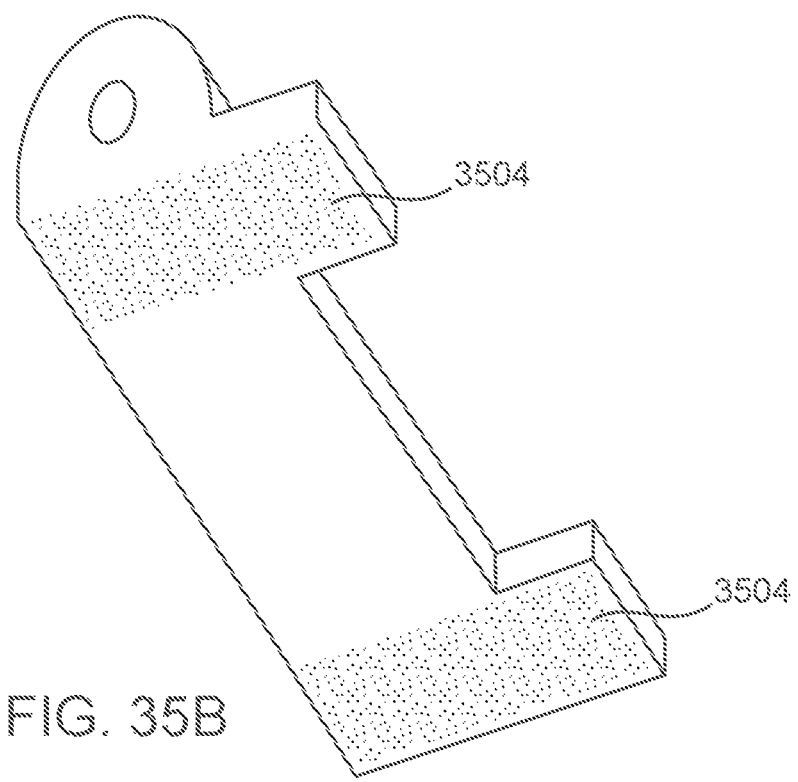

In an embodiment, there is a reinforced bone stabilization device 3500 having a bore hole 3502 through the bridge portion (FIG. 35A). One or more bone engagement features 3504 may also be provided (FIG. 35B).

In an embodiment, the bone fixation to the bone stabilization device is now shown (FIG. 36). Fluorochrome date indicates bone integration without the use of osteogenic stimulants on decorticated bone provides step growth of new bone on the surface of the bone stabilization device 3600. Growth after 2 weeks 3606 can be seen distinctly from growth after four weeks 3604 and six weeks 3602. The test animal was harvested for data analysis after six weeks, and the bone fixation growth was verified through fluorochrome and tissue histology. Bone fixation onto the bone stabilization device was demonstrated on all test animals 100% of the time.

For embodiments described above with respect to fusion of vertebral components, it will be understood that the device can be used as an isolation procedure, or in conjunction with other spine treatment procedures, such as traditional rod and pedicle screw fixation, and interbody fusion device implantation. Also, the device should not require the use of biologics, such as demineralized bone matrix grafts or other bone autografts, bone allografts, bone morphogenic protein (BMP), or related graft materials for successful fusion with bone. In another embodiment, the bone stabilizers may be a bone graft substitute.

Embodiments will now be described with reference to certain specific examples. It will be understood that these examples are illustrative and not meant to be limiting.

Example 1

Preparation of Devices for Implantation

Devices were prepared inhouse from a flat piece of Grade 5 titanium alloy. The devices were cut using a low speed saw and prescribed geometries achieved using a burr.

For bone integration, a three dimensional structure was created on one side of some of the devices at both ends and a porous perforated interface was created at both ends of other devices.

Devices with three different geometries were prepared, all having a three dimensional bone integration surface on one side of the device at both ends. The geometries were similar to those as illustrated in herein.

Figure 16:
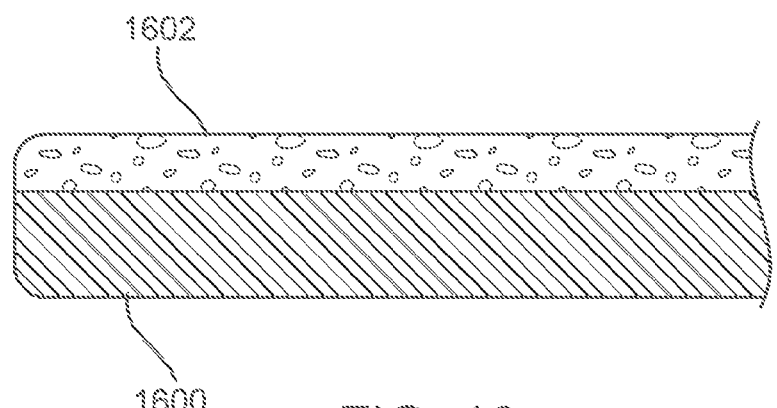
FIG. 16 is a detailed view of the bone stabilizer device of FIG. 15.

The devices with perforated integration surfaces were similar to the device illustrated in FIGS. 15 & 16.

The implants were cleaned in 70% ethanol, allowed to air dry and steam sterilized prior to implantation.

Example 2

Posterolateral Fusions in Rabbits Using the Present Devices 2.1 Materials and Methods 2.1.1 Animals Five skeletally mature New Zealand White Rabbits were purchased through approved suppliers by the University of New South Wales. Animals were housed at the University of New South Wales in approved single cages. Animals were fed a standard diet and continued access to water. Analysis of the feed and water was kept on file at the study site. Animals were individually labeled by microchip as well as identified in their cages by identification cards.

2.1.2 Devices

Three devices, sizes scaled appropriately for rabbits, with geometries and a 3 dimensional bone integration surface as shown herein were used.

2.1.3 Surgical Procedures

A single-level posterolateral intertransverse process fusion was performed bilaterally and adjacent to the vertebral body in the lumbar spine at L5-L6 following approval of the Animal Care and Ethics Committee.

The animals were anesthetized for surgery using isoflurane/oxygen inhalation. A midline incision was made in the skin, and the intermuscular plane between the multifidus and longissimus muscles was developed to expose the L5 and L6 transverse processes as well as the intertransverse membrane. A pneumatic burr (Midas Rex, Medtronic, Memphis, Tenn.) was used to decorticate the dorsal aspect of the transverse processes from the vertebral body laterally for a distance of 10 mm from the vertebral body and pars. One device on each side was placed onto the decorticated surfaces of the transverse processes and attached with 3-0 sutures. No rigid fixation (i.e., no screws) was used. No autologous bone graft or synthetic bone grafts were used. The muscle layers were repositioned over the devices and the skin incisions were closed with 3-0 and 4-0 absorbable suture (Dexon, US Surgical, Norwalk Conn.), respectively.

The animals were monitored daily for the first 7 days following surgery and recorded on postoperative monitoring sheets for each animal. The animals were monitored daily thereafter but only recorded weekly. Cage-side observations included, but not limited to, changes in skin and fur, eyes and mucous membranes, and also respiratory, circulatory, autonomic and central nervous system, somatomotor activity and behavior pattern. There was no postoperative restriction on activity and no supportive orthotic devices were used.

2.1.4 Assessment of Spine Fusion

Animals were euthanized via lethal injection of Lethobarb via cardiac injection following isoflurane inhalation at 6 weeks postoperatively. Spines were harvested and photographed using a digital camera. The general integrity of the skin incision was noted along with the macroscopic reaction of the underlining subcutaneous tissues.

Radiograph: Posteroanterior plain radiographs were taken of the harvested spines using a high resolution device (Faxitron HP, Wheeling, Ill.; settings 24 kV for 45 seconds) using digital film (Agfa).

Micro computed tomography (CT): Micro CT slices were taken for all animals using an Inveon in-vivo Micro CT scanner (Siemens Medical, PA, USA) in order to obtain high resolution images. Spines were scanned and the raw images reconstructed to DICOM data using Siemens software. Images were examined in the axial, sagittal and coronal planes to assess the overall quality of the fusion mass.

Manual palpation: The stability of the fusion mass was assessed by manual palpation in all animals at 6 weeks. The fusion mass was examined for flexion as well as lateral bending. The fusions were graded as either fused or not fused.

Non-destructive mechanical testing: Non-destructive mechanical testing was performed prior to destructive testing to failure in tension to provide multidirectional flexibility testing to provide a kinematic analysis of the rabbit lumbar spine. The lumbar spines were embedded in a low melting point alloy and pure moments (270 Nm) applied in axial rotation (AR), flexion-extension (FE) and lateral bending (LB) using a calibrated servohydraulic testing machine. Motions were detected using infra-red motion sensors. Intact non-operated adult rabbit spines that had no previous surgery were evaluated to provide a comparison.

Histology: Samples were fixed in phosphate buffered formalin for a minimum of 48 hours following mechanic testing. The samples were processed for histology by fixation in cold phosphate buffered formalin for a minimum of 72 hours, with 2 changes of formalin. Following adequate fixation, the surgical sites were cut back with a hack saw to isolate the surgical site and stored in phosphate buffered formalin in labeled containers. Samples were dehydrated through a series of increasing concentrations of ethanol: 70-80-90-96-100%. Samples were placed in glass jars and MMA was added and left to infiltrate for at least 4 days under refrigeration, with the lids tightly closed. The MMA was refreshed and sample jars were placed in a 20° C. water bath to polymerize following the addition of a catalyst.

After the samples hardened, the glass jars were broken and the excess MMA trimmed off. Using a Leica SP1600 saw-microtome, 10-15 micron thick sections was made on the coronal plane of the middle of the defect in the coronal plane. The sections were etched with acidic ethanol (98 ml ethanol 96% and 2 ml HCL 37%) for 1 minute, and stained with methylene blue (Sigma, 1% in borax buffer (0.1M) pH8.5) for 1 minute, followed by basic fuchsine (Sigma, 0.3% in water) for 1 minute. In between the staining solutions, the sections were rinsed with tap water and dried using a blow-dryer.

2.2 Results 2.2.1 Surgery and Harvest

All surgery was completed without incident. All animals recovered well with no adverse events.

2.2.2 Radiographs

Radiographs revealed no implant migration or adverse reactions at 6 weeks, as shown in FIGS. 34 and 35.

2.2.3 Micro CT

Micro CT at 12 6 weeks revealed integration at the host bone margins for all devices, and evidence of new bone growing over the device was also noted.

2.2.4 Mechanical Testing

All animals demonstrated fusion by manual palpation.

Figures 39A, 39B:
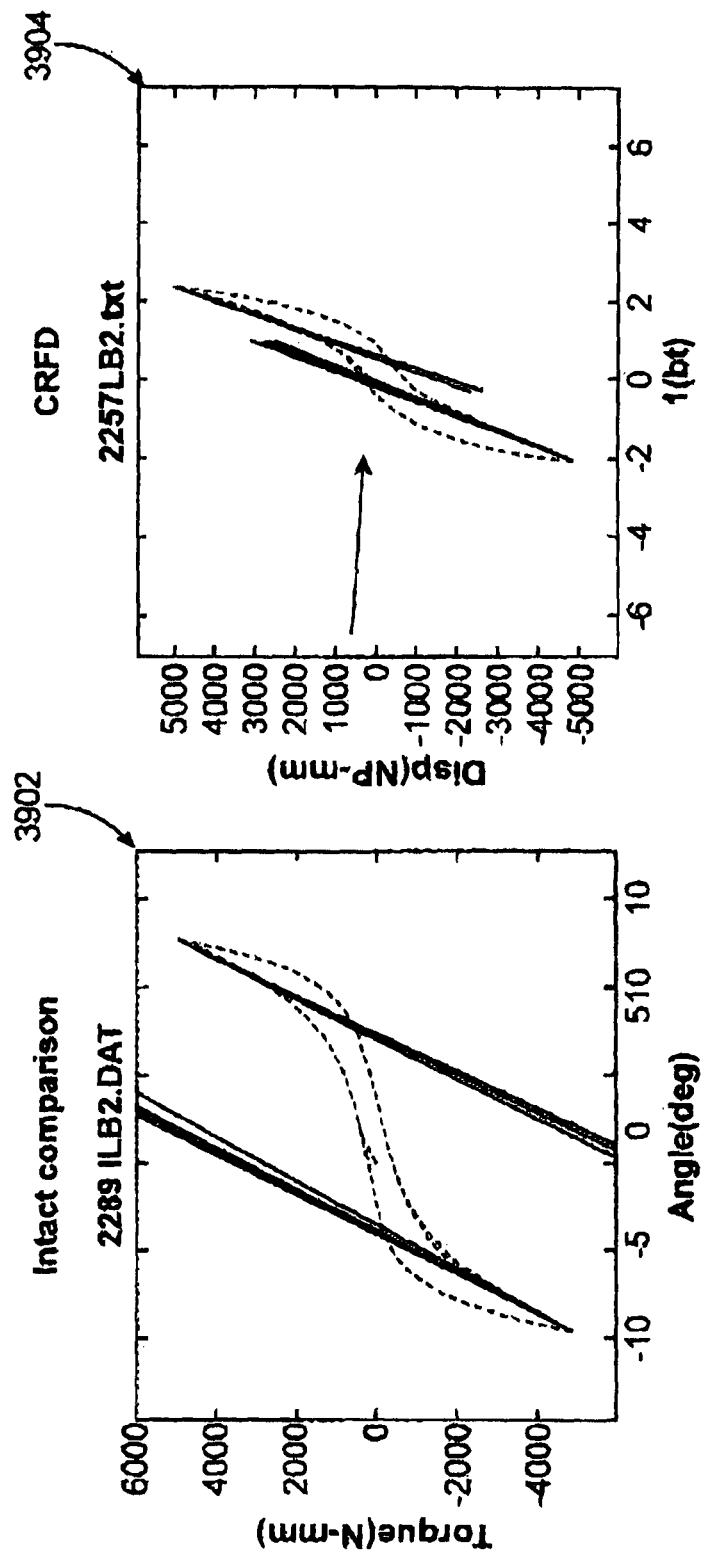
FIGS. 39A, 39B compare a device with intact spine hysteresis curves for lateral bending, all arranged in accordance with at least some embodiments described herein.

Range of motion (ROM) data revealed diminished motion in the 3 axes tested at 6 weeks. More specifically, as shown in FIGS. 39A, 39B, the implanted devices significantly restricted or limited flexion-extension (FE) and lateral bending (LB) as well as changed the axial rotation (AR). Also noteworthy is that the reduced motion was dictated by the geometries design of the devices.

2.2.5 Histology

Typical histology at 6 weeks demonstrated bone integration at the both ends as well as bone growing over the device.

Example 3

Posterolateral Fusion in Sheep Using the Present Devices

Two adult sheep underwent single-level posterolateral intertransverse process fusion and evaluated for fusion following substantially the same protocol as set forth in Example 2.

A flat titanium plate was cut to a parallelogram with a width of 25 mm to match the anatomical angle of the sheep transverse processes. Perforations for bone ingrowth were drilled at 2 mm diameter. Two thicknesses of 1 mm and 2 mm were prepared and tested.

Biomechanical testing results are shown in FIGS. 37A, 37B, 38A, 38B, 39A, and 39B as a hysteresis curve degenerated for each sample in each mode of bending from pure moment testing, wherein the Y axis indicates torque (moment) and the X axis indicates angle. Key parameters taken from these test results include neutral zone, range of motion and stiffness in the linear region. A fitted line was placed on the most linear portion of the curve. This was extended to cross the zero moment line, and delineated the neutral zone. Neutral zone is an important parameter affecting pain. Reduction of this zone decreases the lax portion of the bending curve. This is the portion of the curve where relatively small loads cause large displacements. Range of motion was also taken from these curves. It was calculated as the total angle traveled through positive and the negative moment applications.

Figures 37A, 37B:
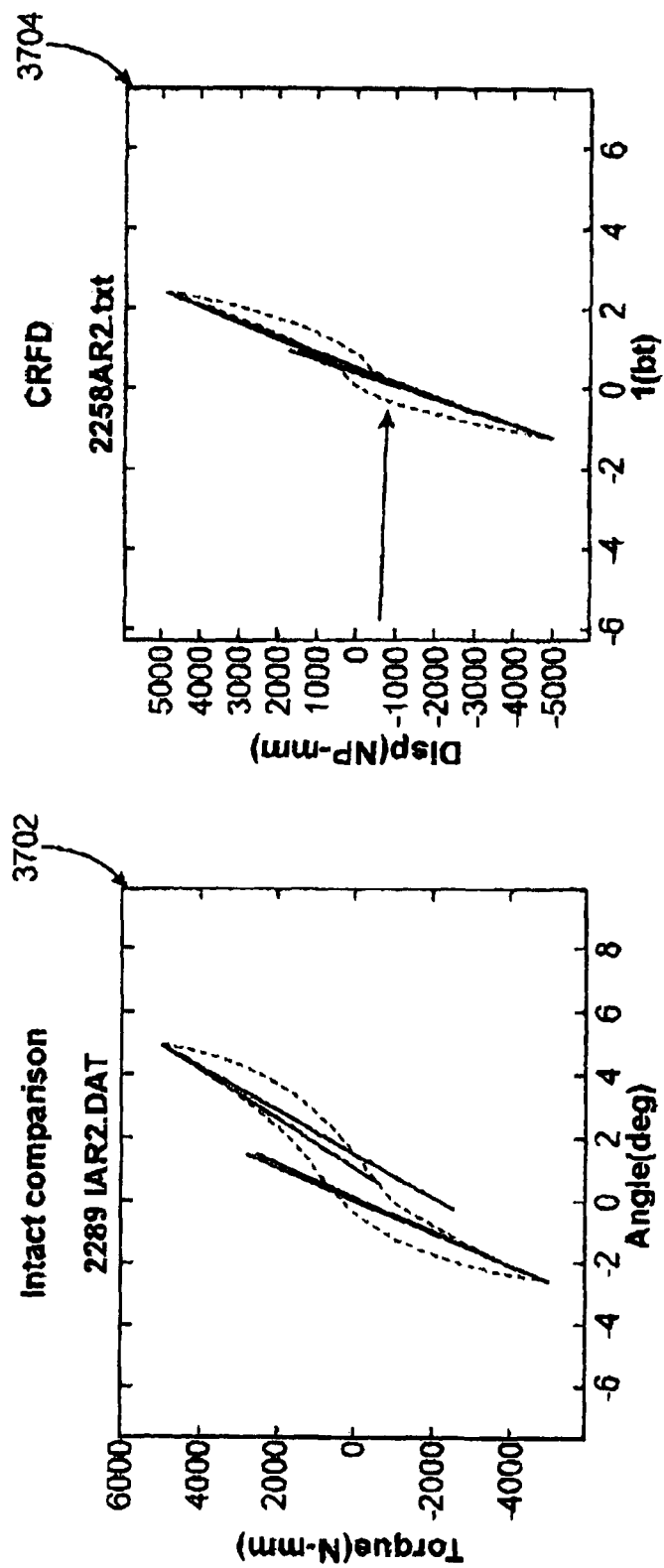
FIGS. 37A, 37B compare a device with intact spine hysteresis curves for axial rotation.
Figures 38A, 38B:
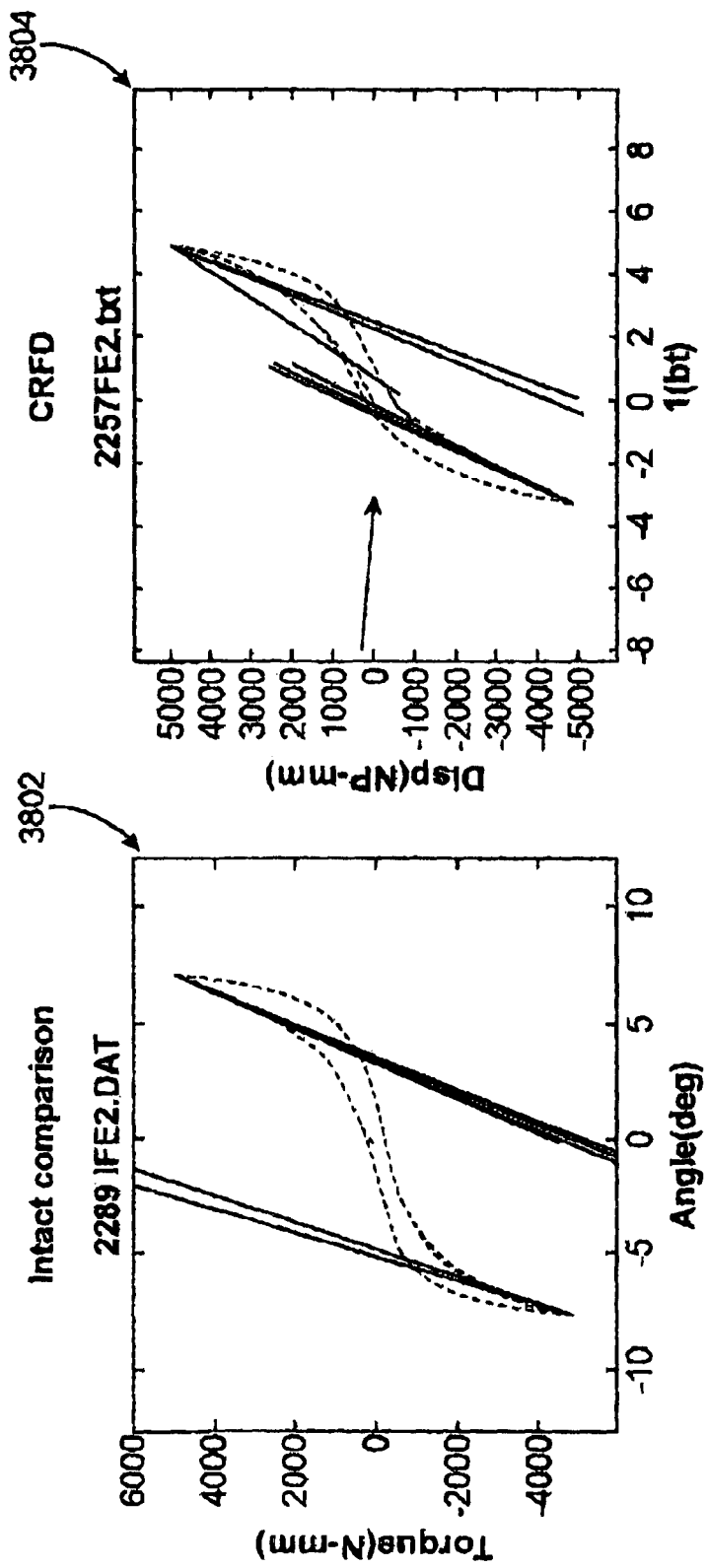
FIGS. 38A, 38B compare a device with intact spine hysteresis curves for flexion extension.

Animal data showing hysteresis curves related to axial rotation are shown for intact spine 3702 and spine with bone stabilization device 3704 (FIGS. 37A, 37B). Animal data showing a hysteresis curve for flexion extension is shown for intact spine 3802 and for treated animal spines 3804 (FIGS. 38A, 38B). Animal data showing hysteresis curves related to lateral bending is shown for intact spine 3902 and for treated spines 3904 (FIGS. 39A, 39B).

With respect to range of motion (ROM), for axial rotation, device placement appears to have an influence, whereas device thickness shows little influence between about 1 and 2 mm; for flexion-extension, device placement appears to have an influence, whereas device thickness suggests some difference between about 1 mm and 2 mm; for lateral bending, device placement appears to have a great deal of influence, whereas device thickness suggests little difference between about 1 mm and 2 mm.

With respect to neutral zone (NZ), for axial rotation, device placement in itself cannot be confirmed, whereas device thickness suggests a great deal of difference between about 1 mm and 2 mm; for flexion-extension, device placement shows a difference, whereas device thickness suggests a great deal of difference between 1 mm and 2 mm; for lateral bending, device placement in shows a great deal influence, whereas device thickness suggests a great deal of difference between about 1 mm and 2 mm.

These results suggest that changing plate thickness affects range of motion and neutral zone selectively in each mode of bending.

Example 4

Proposed Implantation of the Present Devices in Human

The surgical approach used to implant the present devices may vary with design and implanted level. As the present devices may be implanted along with other implants such as interbody implants, it may follow those commonly used approaches to place spinal implants, providing convenient access. All these procedures are performed under general anesthesia with the assistance of X-ray or fluoroscopic guidance. The procedures vary for each individual level in terms of the specific anatomy that is going to be affected.

The present devices may be placed in various target locations around spine, including, but not limited to, transverse process, spinous process, vertebral body, intervertebral space, facet joint, lamina, etc., depending on its intended use. The selection of appropriate devices, as well as the location for placement and anchoring sites, may comprise part of the planning before or during the surgery. Decortication of the target bone may be performed if necessary. The present devices may be restrained by geometry, surrounding anatomy, sutures or screws as desired.

4.1 Lumbar Approaches 4.1.1 Anterior Lumbar Interbody Fusion (ALIF)

As an anterior approach, the lumbar spine is approached from the stomach. An incision is made through the skin and fascia and retracted to one side. The abdominal contents are retracted with the peritoneum intact. The great vessels are retracted to one side and the anterior portion of the spine is visible. From this point, the bone can be prepped to accept the present device. The mounting locations best suited for an anterior approach would be the anterior and lateral aspects of the vertebral bodies. If performed in conjunction with ALIF device, it may be possible to perform the discectomy and access the transverse processes, anterior lamina, and other posterior structures prior to placing the final interbody implant.

4.1.2 Posterior Lumbar Interbody Fusion (PLIF)

In a posterior approach, the spine is approached from the back. The patient is placed in the prone position. An incision is made along the midline. Fascia and muscles are divided and retraction allows visualization of the posterior elements. A laminectomy and facetectomy are often performed as part of a spinal fusion procedure to allow access to the interbody space and to decompress nerves. This procedure could also provide an anchorage point for the present devices.

4.1.3 Transforaminal Lumbar Interbody Fusion (TLIF)

As part of a TLIF the approach is still posterior; however, the surgery is performed unilaterally. This approach is well suited to the present devices placed on the transverse processes.

4.1.4 Direct Lateral Interbody Fusion (DLIF) or eXtreme Lateral Interbody Fusion (XLIF)

XLIF and DLIF approaches represent lateral access. The lateral incision provides access to the underlying soft tissues and the psoas muscle which may be mobilized or separated to provide access to the spine. Access is provided with a tube like instrument with dilators to provide minimal tissue disruption. All approaches can be done with this minimally invasive method. The target may be the disc, the lateral portion of the vertebral body or the transverse processes.

4.2 Cervical Approaches 4.2.1 Anterior Cervical Disc Fusion (ACDF)

Anterior approaches to the cervical spine require a horizontal skin incision to the neck, mobilization to the musculature and retraction of the trachea, esophagus, and vasculature. This approach may be used for anterior placement on the vertebral body, transverse processes or tubercles of the transverse processes.

4.2.2 Posterior Cervical Fusion (PCF)

The approach used for posterior cervical fusion includes a midline incision on the back of the neck directly over the affected level. Fascia and musculature are divided exposing the spinous processes of the vertebrae. A laminectomy and foraminotomy may be performed. This approach allows the placement of the present devices to be on the spinous processes, interlaminally, or between the transverse processes.

4.3 Minimally Invasive Surgery (MIS)

An MIS approach as is used for pedicle screws and rods implantation includes image intensification and the following steps: marking the position of the lateral aspect of the pedicle or transverse process depending on the target on the skin; incising the skin; placing a cannulated needle through the skin incision and "docking" onto the desired implant location; and preparing the bone surface. This may be done with an instrument, which rasps or otherwise disturbs the periosteum. Alternatively, the periosteum may be left in place and the implant itself may prepare the periosteum. And no other optional procedure may be the use of dilator tubes, to gain a larger access.

While the embodiments described herein have been illustrated and described in detail in the foregoing description, the same is to be considered as illustrative and not restrictive in character, it being understood that only certain embodiments have been shown and described and that all changes and modifications that come within the spirit of the devices and methods are desired to be protected.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A bone stabilization device comprising:
   a body comprising:
      a first cup adapted to rest on a first transverse process of a first vertebrae, the first cup having a bone engagement feature configured to be secured to the first transverse process without use of a screw;
      a second cup adapted to rest on a second transverse process of a second vertebrae; and
      a bridge portion extending between the first cup and the second cup, at least a portion of the bridge portion adapted to be positioned between the first transverse process and the second transverse process in use,
   wherein the bridge portion has a rigidity of about $5.5 \times 10^{-4}$ Nm$^2$ or higher,
   wherein the bridge portion comprises a planar body arranged at least one of parallel to or coplanar with a plane defined by the first and second transverse processes; and wherein the body is devoid of through holes.

2. The device of claim 1, wherein each of the first cup and the second cup comprises a bone integration feature.

3. The device of claim 2, wherein the bone integration feature of the second cup comprises a fastener.

4. The device of claim 3, wherein at least one of the bone integration feature of the first cup or the bone integration feature of the second cup is adapted to trigger an osteogenic response in a bone.

5. The device of claim 1, wherein the bridge portion is narrower than either or both of the first and second cups with respect to an axis of the bone stabilization device between the first cup and the second cup.

6. The device of claim 5, wherein the bridge portion is located toward a side of the bone stabilization device.

7. The device of claim 1, wherein the body comprises two or more different materials selected from: a polymer, a metal, and an alloy material.

8. The device of claim 7, wherein the two or more different materials include a first polymer and a second polymer, and wherein the first polymer and the second polymer are chosen from a group comprising: polyetheretherketone (PEEK) and modified PEEK.

9. The device of claim 1, wherein the body has a rigidity of about $9 \times 10^{-3}$ Nm$^2$ or higher.

10. The device of claim 1, wherein the body consists at least partially of titanium.

11. The device of claim 1, wherein at least one of:
    the rigidity is with respect to the body; or
    the body is substantially flat.

12. The device of claim 1, wherein the bridge portion has a lower aspect ratio than at least one of the first cup or the second cup.

13. The device of claim 1, wherein the bone engagement feature is capable of receiving bone ingrowth, ongrowth and/or through growth.

14. The device of claim 1, wherein the body further comprises a reinforcement element that includes biocompatible metal or metal alloy and the bridge portion comprises a polymer.

15. The device of claim 1, further comprising a biochemical and/or biological agent for stimulation of bone growth.

16. The device of claim 1, wherein the bone engagement feature comprises a textured surface or a plurality of perforations.

17. The device of claim 1, wherein the body has an edge of a thickness of 1-2 mm.

18. The device of claim 1, wherein the bridge portion comprises a bone engagement portion on at least a portion thereof.

19. A bone graft substitute comprising:

a body comprising:

a first cup adapted to receive therein a portion of a first transverse process of a first vertebrae, the first cup having a bone engagement feature configured to be secured to the first transverse process without use of a screw;

a second cup adapted to receive therein a portion of a second transverse process of a second vertebrae; and a bridge portion connecting the first cup and the second cup, the bridge portion adapted to be positioned between the first transverse process and the second transverse process in use;

wherein the bone engagement feature is configured for fusion with a damaged bone surface absent bone graft material and the body is adapted to withstand relative flexion movement of the first and second transverse processes when the first and second cups become fused to the first and second transverse processes, and wherein the bridge portion has a rigidity of about $5.5 \times 10^{-4}$ Nm$^2$ or higher, wherein the bridge portion comprises a planar body arranged at least one of parallel to or coplanar with a plane defined by the first and second transverse processes.

20. A spinal fusion system comprising:

a first bone stabilization device that includes:

a first bridge;

a first cup at a first end of the first bridge and configured to engage a left transverse process of a first vertebrae;

a second cup at a second end of the first bridge opposite the first end of the first bridge and configured to engage a left transverse process of a second vertebrae adjacent to the first vertebrae;

a second bone stabilization device that includes:

a second bridge;

a third cup at a first end of the second bridge and configured to engage a right transverse process of the first vertebrae;

a fourth cup at a second end of the second bridge opposite the first end of the second bridge and configured to engage a right transverse process of the second vertebrae;

wherein:

each of the first bridge and second bridge comprises a flat-plate main body with two opposite edges that extend between the first end and the second end;

the two opposite edges of the flat-plate main body of each of the first bridge and the second bridge have different curvatures from each other in which:

a medial edge of each flat-plate main body is straight and an outer edge of each flat-plate main body has a concave curvature; or an outer edge of each flat-plate main body is straight and a medial edge of each flat-plate main body has a convex curvature.

* * * * *

UNITED STATES PATENT AND TRADEMARK OFFICE
CERTIFICATE OF CORRECTION

PATENT NO. : 9,931,143 B2
APPLICATION NO. : 14/424408
DATED : April 3, 2018
INVENTOR(S) : Walsh et al.

It is certified that error appears in the above-identified patent and that said Letters Patent is hereby corrected as shown below:

In the Specification

In Column 1, Line 15, delete "sugically" and insert -- surgically --, therefor.

In Column 19, Line 5, delete "Wheeling, Ill.;" and insert -- Wheeling, IL; --, therefor.

Signed and Sealed this
Fifth Day of June, 2018

Andrei Iancu
*Director of the United States Patent and Trademark Office*